United States Patent
Kleiner et al.

(10) Patent No.: US 6,375,978 B1
(45) Date of Patent: Apr. 23, 2002

(54) RATE CONTROLLING MEMBRANES FOR CONTROLLED DRUG DELIVERY DEVICES

(75) Inventors: Lothar W. Kleiner; Robert M. Gale, both of Los Altos; Randall G. Berggren, Livermore; Gilbert T. Tong, Union City; Guohua Chen, Sunnyvale, all of CA (US); Keith E. Dionne, Cambridge, MA (US); Paul R. Houston, Hayward, CA (US)

(73) Assignee: ALZA Corporation, Mountain View, CA (US)

( * ) Notice: Subject to any disclaimer, the term of this patent is extended or adjusted under 35 U.S.C. 154(b) by 0 days.

(21) Appl. No.: 09/213,213

(22) Filed: Dec. 17, 1998

Related U.S. Application Data

(60) Provisional application No. 60/068,377, filed on Dec. 22, 1997.

(51) Int. Cl.$^7$ .............................. A61K 9/70; A61K 9/24
(52) U.S. Cl. ...................... 424/449; 424/424; 424/448; 424/473
(58) Field of Search ................................ 424/444, 448, 424/449, 422, 423, 424, 473

(56) References Cited

U.S. PATENT DOCUMENTS

| | | | |
|---|---|---|---|
| 3,788,322 A | 1/1974 | Michaels | 128/260 |
| 3,797,494 A | 3/1974 | Zaffaroni | 128/268 |
| 3,845,770 A | 11/1974 | Theeuwes et al. | 128/260 |
| 3,916,899 A | 11/1975 | Theeuwes et al. | 128/260 |
| 3,987,790 A | 10/1976 | Eckenhoff et al. | 128/260 |
| 4,031,894 A | 6/1977 | Urquhart et al. | 128/268 |
| 4,111,202 A | 9/1978 | Theeuwes | 128/260 |
| 4,111,203 A | 9/1978 | Theeuwes | 128/260 |
| 4,201,211 A | 5/1980 | Chandrasekaran et al. | 128/268 |
| 4,203,439 A | 5/1980 | Theeuwes | 128/260 |
| 4,327,725 A | 5/1982 | Cortese et al. | 128/260 |
| 4,379,454 A | 4/1983 | Campbell et al. | 604/897 |
| 4,436,741 A | 3/1984 | Urquhart et al. | 424/267 |
| 4,588,580 A | 5/1986 | Gale et al. | 424/21 |
| 4,612,008 A | 9/1986 | Wong et al. | 604/892 |
| 4,615,699 A | 10/1986 | Gale et al. | 604/897 |
| 4,661,105 A | 4/1987 | Gale | 604/897 |
| 4,681,584 A | 7/1987 | Gale et al. | 604/897 |
| 4,698,062 A | 10/1987 | Gale et al. | 604/896 |
| 4,725,272 A | 2/1988 | Gale | 424/448 |
| 4,832,953 A | 5/1989 | Campbell et al. | 424/448 |
| 4,865,845 A | 9/1989 | Eckenhoff et al. | 424/424 |
| 4,908,027 A | 3/1990 | Enscore et al. | 604/890.1 |
| 4,931,285 A | 6/1990 | Edgren et al. | 424/473 |
| 5,004,610 A | 4/1991 | Osborne et al. | 424/448 |
| 5,024,842 A | 6/1991 | Edgren et al. | 424/473 |
| 5,034,229 A | 7/1991 | Magruder et al. | 424/422 |
| 5,057,318 A | 10/1991 | Magruder et al. | 424/438 |
| 5,059,423 A | 10/1991 | Magruder et al. | 424/438 |
| 5,110,596 A | 5/1992 | Magruder et al. | 424/438 |
| 5,112,614 A | 5/1992 | Magruder et al. | 424/422 |
| 5,137,727 A | 8/1992 | Eckenhoff | 424/422 |
| 5,160,743 A | 11/1992 | Edgren et al. | 424/473 |
| 5,234,692 A | 8/1993 | Magruder et al. | 424/473 |
| 5,234,693 A | 8/1993 | Magruder et al. | 424/473 |
| 5,310,559 A | 5/1994 | Shah et al. | 424/448 |
| 5,342,623 A | 8/1994 | Enscore et al. | 424/448 |
| 5,344,656 A | 9/1994 | Enscore et al. | 424/448 |
| 5,364,630 A | 11/1994 | Osborne et al. | 424/449 |
| 5,728,396 A | * 3/1998 | Peery et al. | 424/422 |

FOREIGN PATENT DOCUMENTS

| | | | |
|---|---|---|---|
| EP | 551 698 A1 | 7/1993 | A61K/9/00 |
| WO | 97/20550 | 6/1997 | A61K/9/70 |
| WO | 97/27840 | 8/1997 | A61K/9/00 |

* cited by examiner

Primary Examiner—Shelley A. Dodson
(74) Attorney, Agent, or Firm—Vandana Date

(57) ABSTRACT

This invention provides rate controlling membranes for controlled drug delivery devices that are stable over time and exhibit more predictable and consistent membrane functionality. According to another aspect, the membranes have enhanced permeability. According to the invention, the rate controlling membrane of a controlled drug delivery device is subjected to a pre-treatment annealing process wherein it is subjected to an elevated temperature for a predetermined time period and subsequently cooled to ambient conditions before incorporation into a controlled drug delivery device.

35 Claims, 14 Drawing Sheets

RATE CONTROLLING MEMBRANES FOR CONTROLLED DRUG DELIVERY DEVICES

RELATED APPLICATIONS

This application claims the benefit of U.S. Provisional Application No. 60/068,377, filed on Dec. 22, 1997.

FIELD OF THE INVENTION

This invention relates to the field of drug delivery devices which incorporate a rate controlling membrane in order to control the rate of release of a drug from the device to a patient. More particularly, the invention is directed to rate controlling membranes for drug delivery devices characterized by being subjected to an annealing process in accordance with the present invention. The rate controlling membranes of this invention exhibit improved membrane functionality particularly with respect to storage time.

BACKGROUND OF THE INVENTION

The use of rate controlling membranes to control delivery of a drug from a drug delivery device is well known. For example, transdermal drug delivery devices including rate controlling membranes are disclosed in U.S. Pat. Nos. 3,797,494, 4,031,894, 4,201,211, 4,379,454, 4,436,741, 4,588,580, 4,615,699, 4,661,105, 4,681,584, 4,698,062, 4,725,272, 4,832,953, 4,908,027, 5,004,610, 5,310,559, 5,342,623, 5,344,656, and 5,364,630, which are incorporated in their entirety herein by reference. As disclosed in these patents, various materials, including ethylene vinyl acetate copolymers and polyethylene, may be used to form rate controlling membranes useful for transdermal drug delivery systems. Additional materials useful for forming rate controlling membranes for transdermal drug delivery devices are disclosed in K. P. R. Chowdary et al. "Preparation and Evaluation of Cellulose Acetate Films as Rate Controlling Membranes for Transdermal Use" Indian Drugs 29 (7).

For a selected membrane material, after conversion of the polymer pellet to the membrane, the necessary rate control for a transdermal drug delivery device is provided by varying the composition, pore size, or thickness of the rate controlling membrane, adjusting the viscosity of the drug formulation to be administered by appropriate formulation, or impregnating the pores of the membranes with a diffusive medium as disclosed in U.S. Pat. No. 3,797,494 listed above. The rate controlling membrane is then incorporated into a transdermal drug delivery device without any other additional treatment thereof.

Diffusional and osmotically driven fluid-imbibing dosage forms incorporating rate controlling membranes are also known in the art. For example, U.S. Pat. Nos. 3,845,770 and 3,916,899, incorporated herein by reference, disclose a device comprising a wall that surrounds a compartment containing a drug for delivery to a patient. The wall of the device is permeable to the passage of fluid. Drug is released from the device by fluid being imbibed through the wall into the device at a rate determined by the permeability of the wall and the osmotic pressure gradient across the wall. Other diffusional and osmotic fluid-imbibing dosage forms are disclosed in U.S. Pat. Nos. 3,987,790, 4,111,202, 4,111,203, 4,203,439, 4,327,725, 4,612,008, 4,865,845, 5,034,229, 5,057,318, 5,059,423, 5,110,596, 5,112,614, 5,137,727, 5,234,692, and 5,234,693, all of which are hereby incorporated in their entirety by reference.

Additionally, U.S. Pat. Nos. 4,931,285, 5,024,842, and 5,160,743 disclose a dosage form comprising a coat surrounding a drug. The coat comprises a water soluble overcoat polymer and a subcoat. The overcoat and the subcoat are annealed to provide a continuous, insoluble membrane or film that surrounds the drug and which dissolves in an aqueous environment of use.

One problem associated with prior art rate controlling membranes formed from thermoplastic polymers is that they often encounter morphological changes after processing over long periods of time due to phase separation of domain structures. These morphological changes can alter the membrane functionality. For example, the water permeation or water uptake rate through the membrane of fluid-imbibing devices may vary over time, leading to inconsistent performance of the device.

Another problem associated with prior art rate non-annealed rate controlling membranes used in controlled drug delivery devices is that the permeability of the membrane may vary over the storage period, particularly when such devices are exposed to elevated temperatures. If this occurs, the system would not have a drug release rate which is stable as a function of storage time. This is particularly undesirable where, for example, the permeability of the rate controlling membrane to the drug is increased beyond a preferred range due to exposure of the system to elevated temperatures.

Variations in the rate of administration of drugs can effect efficacy and cause undesirable side effects. As can be appreciated by one of ordinary skill in the art, variations in the functionality of rate controlling membranes of drug delivery devices over storage may arise in any device which incorporates a rate controlling membrane and can pose a significant problem.

BRIEF DESCRIPTION OF TERMS

As used herein, the term "drug" is to be construed in its broadest sense to mean any material which is intended to produce some biological, beneficial, therapeutic, or other intended effect, such as permeation enhancement, for example, on the organism to which it is applied.

As used herein, the term "individual" intends a living mammal and includes, without limitation, humans and other primates, livestock and sports animals such as cattle, pigs and horses, and pets such as cats and dogs.

As used herein, the term "membrane functionality" refers to properties of the membrane which affect the desired degree of rate control of the drug delivery device in which the membrane is used and includes for example, drug permeability, water permeability, and/or water uptake.

As used herein, the term "transdermal" intends both percutaneous and transmucosal administration, i.e., passage of drug through skin or mucosal tissue into the systemic circulation.

SUMMARY OF THE INVENTION

According to this invention, rate controlling membranes intended for use in controlled drug delivery devices are pretreated by an annealing process prior to or subsequent to incorporation of the membrane into the drug delivery device. The annealing process of this invention provides rate controlling membranes which exhibit consistent membrane functionality over time. In one embodiment, the annealed rate controlling membranes of this invention comprise enhanced permeability compared to non-annealed membranes that is more predictable with respect to thermal transients, particularly throughout storage over time. According to another embodiment, rate controlling membranes subjected to the annealing process of this invention maintain a permeability within a preferred range even after being subjected to elevated temperatures.

Accordingly, it is an aspect of this invention to provide rate controlling membranes for use in controlled drug delivery devices that overcome the disadvantages associated with those of the prior art.

Another aspect of the invention is to provide rate controlling membranes which exhibit consistent membrane functionality over time.

Another aspect of this invention is to provide rate controlling membranes for transdermal drug delivery systems that have more predictable drug permeabilities with respect to thermal transients.

Another aspect of this invention is to provide rate controlling membranes for transdermal drug delivery devices that have drug permeabilities that are stable as a function of storage time.

Another aspect of this invention to provide rate controlling membranes for transdermal drug delivery devices that provide enhanced drug permeability.

Yet another aspect of this invention is to provide rate controlling membranes for fluid-imbibing drug delivery devices which exhibit consistent water permeability and water uptake over a storage period.

Therefore, the invention comprises the following aspects, either alone or in combination:

A rate controlling membrane for a controlled drug delivery device characterized by being subjected to an elevated temperate of about 300° C. to about 5° C. below the melting temperature of the membrane polymer for a predetermined period of about 1–250 hours and subsequently incorporated into the delivery device.

The membrane material may be selected from the group consisting of ethylene vinyl acetate copolymers, polyethylene, copolymers of ethylene, polyolefins including ethylene oxide copolymers such as Engage® (DuPont Dow Elastomers), polyamides, cellulosic materials, polyurethanes, polyether blocked amides copolymers such as PEBAX® (Elf Atochem North America, Inc.), and polyvinyl acetate.

The device may be a transdermal drug delivery device comprising a drug reservoir layer between a backing layer and a contact adhesive layer, wherein rate controlling membrane is on the skin-proximal side of the drug reservoir layer. The drug reservoir may also contain one or more permeation enhancers and/or other excipients.

The device may be a transdermal drug delivery device comprising a backing layer, a permeation enhancer reservoir containing a permeation enhancer on the skin proximal side of the backing layer, a drug reservoir layer containing at least one drug to be transdermally administered on the skin proximal side of the permeation enhancer reservoir, and a means for maintaining said drug device in drug transmitting relation with the skin, wherein the rate controlling membrane is positioned between the permeation enhancer reservoir and the drug reservoir.

Alternatively, the membrane may be positioned in sealing relationship with an internal surface of one end of an impermeable reservoir of a fluid-imbibing drug delivery device, wherein the fluid imbibing drug delivery device comprises an impermeable reservoir containing a piston that divides the reservoir into a drug containing chamber and a water-swellable agent containing chamber, wherein the water-swellable agent containing chamber is provided with an outlet which accommodates the membrane. The agent containg layer may comprise leuprolide.

The membrane may be cooled to ambient conditions before being incorporated into the delivery device.

Additionally, the invention is directed to a method for processing rate controlling membranes used in controlled drug delivery devices comprising:

a) exposing the membrane to a predetermined temperature of from about 30° C. to about 5° C. below the melting temperature of the membrane polymer;

b) maintaining the membrane at the predetermined temperature for a period of time of from about 1 to 250 hours; and c) incorporating said membrane into a controlled drug delivery device.

These and other aspects, features, and advantages of this invention will be more apparent from the following detailed description and drawings.

DETAILED DESCRIPTION OF THE INVENTION

According to this invention, rate controlling membranes for controlled drug delivery systems are subjected to an annealing process which comprises subjecting the rate controlling membranes to an annealing temperature ($T_a$) for a specified time after conversion of the polymer pellet to the membrane or during the conversion process itself. The membranes are maintained at the annealing temperature for a predetermined period of time, and subsequently cooled to ambient conditions over a time period ranging from 0.1 to 150 hours, preferably 0.1–48 hours. The membranes are then incorporated into a controlled drug delivery system.

Proper annealing conditions are selected in accordance with the particular polymer membrane based upon its thermal properties including its glass transition temperature, $T_g$, and melting point, $T_m$, molecular weight, molecular weight distribution, and crystallization kinetics. A wide range of annealing conditions can be selected. The annealing temperature $T_a$ is above $T_g$ and below $T_m$ of the membrane material. The most rapid annealing process occurs at a $T_a$ halfway between $T_g$ and $T_m$. The largest crystal formation is observed at a $T_a$ just below $T_m$. The preferred annealing temperature according to this invention is within the range of above about 30° C. and at least 5° C. below $T_m$ of the polymer membrane material, more preferably about 45° C. to 80° C. The membrane is preferably maintained at the annealing temperature for a period of time of about 1 to 250 hours, more preferably about 1 to 75 hours. According to a preferred embodiment, it is preferable to allow the membrane to set at room temperature for relaxation for a predetermined period prior to the annealing step.

A preferred embodiment is directed to rate controlling membranes that are more predictable with respect to thermal transients. According to this embodiment, the permeability of rate controlling membranes subjected to the annealing process of this invention is maintained below a predetermined maximum level after exposure of the system to thermal transients. Membrane annealing according to this embodiment provides predetermined delivery rates for predetermined administration intervals within an overall administration period.

A particularly preferred embodiment according to this aspect of the invention is directed to rate controlling membranes comprising an ethylene vinyl acetate (EVA) copolymer. The desired membrane permeability is achieved by proper selection of the vinyl acetate (VA) content of the copolymer in addition to selection of the proper annealing conditions. In general, the membrane permeability decreases as the VA content of an EVA membrane decreases. Preferred annealing conditions according to this embodiment comprise an annealing temperature of about 45–75° C., most preferably about 52° C.–72° C., for a period of about 1 hour–72 hours, most preferably 2–36 hours, and a VA content of 4–18%, most preferably 5–12%.

Figure 5:
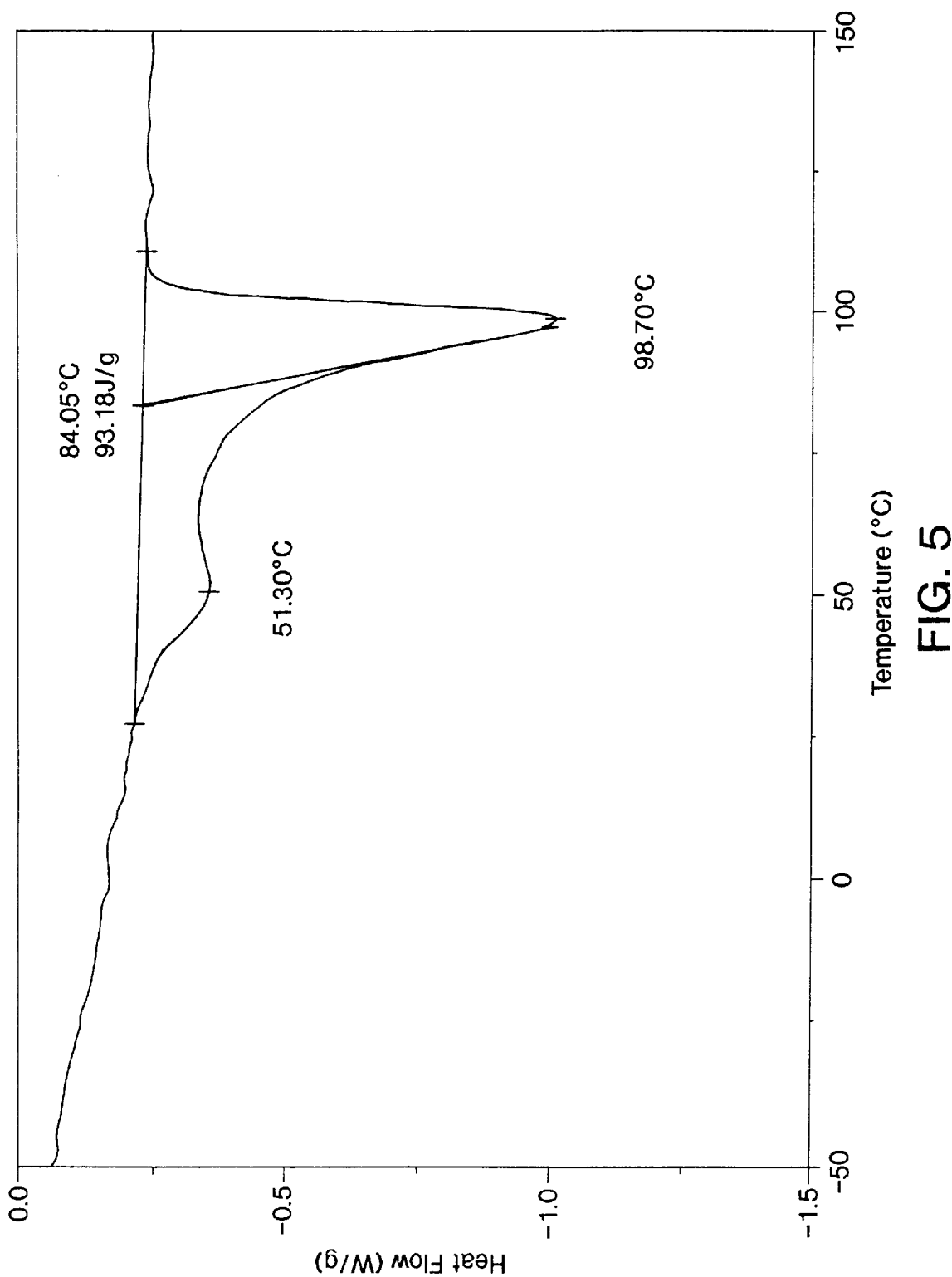
FIG. 5 is a DSC profile for a non-annealed ethylene vinyl acetate film comprising 9% vinyl acetate wherein the DSC profile is examined at a temperature range of —50–150° C. heated at a rate of 10° C./min.
Figure 6:
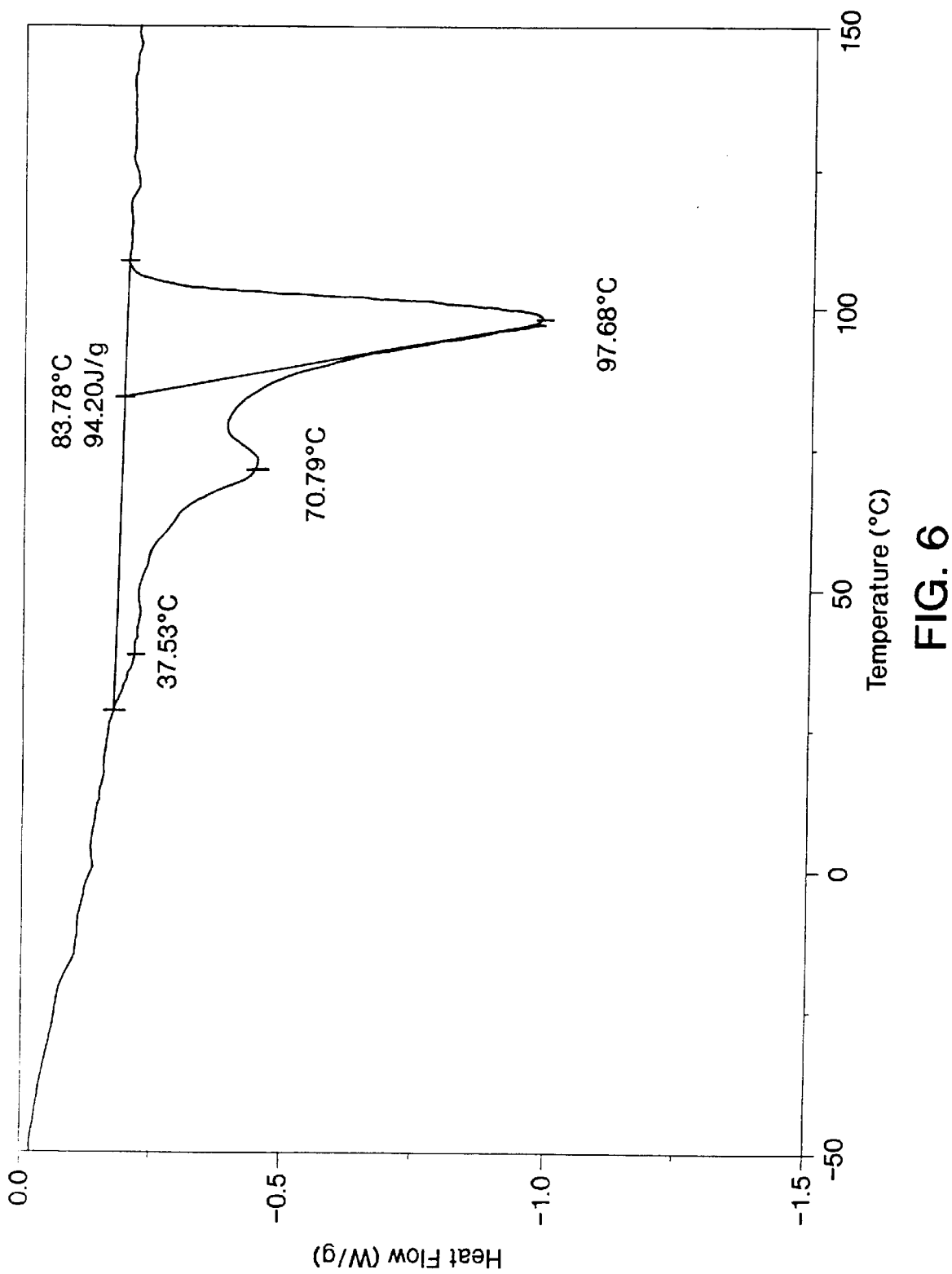
FIG. 6 is a DSC profile for an annealed ethylene vinyl acetate film comprising 9% vinyl acetate wherein the DSC profile is examined at a temperature range of —50–150  C. heated at a rate of 10° C./min.

Differential scanning calorimetry (DSC) analysis may be used to determine the extent of membrane annealing and may be performed by procedures well known in the art. According to the preferred embodiments comprising an EVA copolymer rate controlling membrane, significant changes in the DSC profile are noted at annealing temperatures greater than about 60° C. At these temperatures, as seen in FIGS. 5 and 6, the primary peak ($T_m$) is observed at about 98° C. and remains substantially consistent at various annealing temperatures. However, the secondary peak, observed to appear at about 51° C. for a non-annealed EVA membranes (9% vinyl acetate) (FIG. 5), appears at a higher temperature upon annealing at temperatures of about 40° C. and greater (second peak at 71° C. for an EVA (9% vinyl acetate) membrane annealed at 60° C. for 2 hours as seen in FIG. 6). Preferred embodiments for EVA copolymer rate controlling membranes are directed to rate controlling membranes exhibiting DSC profiles having the secondary peak at a temperature within the range of about 51–80° C., most preferably 56–75° C. Additionally, a third, less significant peak is observed for annealed EVA, preferably within the range of about 32–40° C.

According to the preferred embodiments comprising polyurethane membranes, DSC analysis showed that an increase in annealing temperature caused a slight increase in the melting temperature. Similarly, a slight increase in moisture content from 0 to 1% caused a slight increase in melting temperature. It is preferred according to this embodiment to anneal at dry conditions.

Rate controlling membranes subjected to the annealing process of this invention overcome the disadvantages of those of the prior art. According to one embodiment, membrane annealing according to this invention surprisingly results in rate controlling membranes having enhanced permeabilities to drugs compared to membranes not treated in accordance with this invention. This is contrary to expectations of lower drug permeabilities due to the higher density of the annealed rate controlling membrane. For example, the density and crystallinity of a polymer are among the factors influencing the polymer's permeability coefficient. In general, the higher the density and crystallinity, the lower the permeability coefficient and the resulting membrane permeability. See "Permeability and Diffusion Data" Polymer Handbook, 3rd Edition, J. Bradley & E. H. Immergut, J. Wiley, 1989, p. 435. While not being limited to any particular theory, the inventor's believe that, according to this embodiment, the annealing process of this invention enhances significantly the mobility of the amorphous phase interconnecting the crystalline regions of the annealed membranes, thus leading to the enhanced permeability observed from the annealed membranes.

Figure 1:
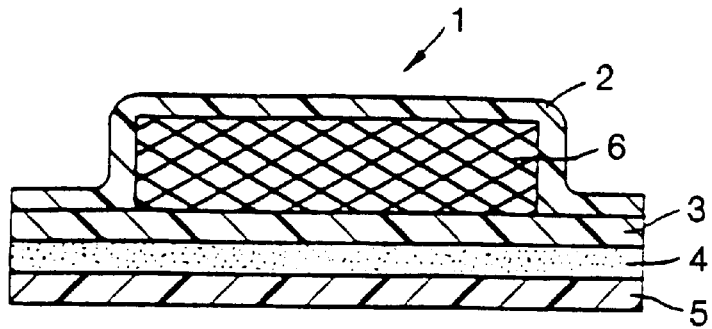
FIG. 1 is a cross-sectional view of one embodiment of a transdermal therapeutic drug delivery device which may be used in accordance with the present invention.

A preferred embodiment of the present invention is directed to rate controlling membranes used in transdermal drug delivery devices as shown in FIG. 1. In FIG. 1, a transdermal therapeutic system 1 according to this invention comprises a pouch formed from an impermeable backing 2, rate controlling membrane 3, and a contact adhesive layer 4, covered by a removable protective release liner 5. The impermeable backing is configured to provide a central volume which contains a drug reservoir 6 in the form of a gel having dissolved and suspended drug therein. Means other than the in-line contact adhesive layer 4 may be used for maintaining the system on the skin such as a peripheral ring of adhesive outside the path of drug flow from the system to the skin. Adhesive overlays or other fastening means such as belts and elastic arm bands are also contemplated.

Figure 2:
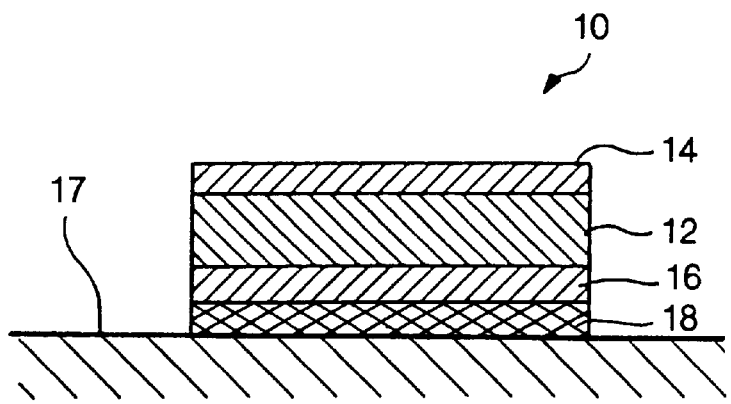
FIG. 2 is a cross-sectional view of another embodiment of a transdermal therapeutic drug delivery device which may be used in accordance with the present invention.

Referring now to FIG. 2, a multilaminate type of transdermal therapeutic system according to this invention is shown. Device 10 comprises a drug reservoir 12 preferably in the form of a matrix containing both the drug and a permeation enhancer, if used, dispersed therein. Reservoir 12 is sandwiched between a backing layer 14, which is preferably impermeable to both the drug and the permeation enhancer mixture, and rate controlling membrane 16. In FIG. 2, the drug reservoir 12 is formed of a material, preferably a polymeric material, that is sufficiently viscous to maintain its shape. The device 10 adheres to the surface of the skin 17 by means of the contact adhesive layer 18.

With certain formulations, an adhesive overlay or other fastening means may be preferable to the in-line contact adhesive. The adhesive for layer 18 should be chosen so that it is compatible with system components and the skin and does not interact with the drug or other system component in any way to alter functionality. The adhesive layer 18 may optionally contain enhancer and/or drug. A removable liner (not shown) is normally provided along the exposed surface of adhesive layer 18 and is removed prior to application of device 10 to the skin 17.

Figure 3:
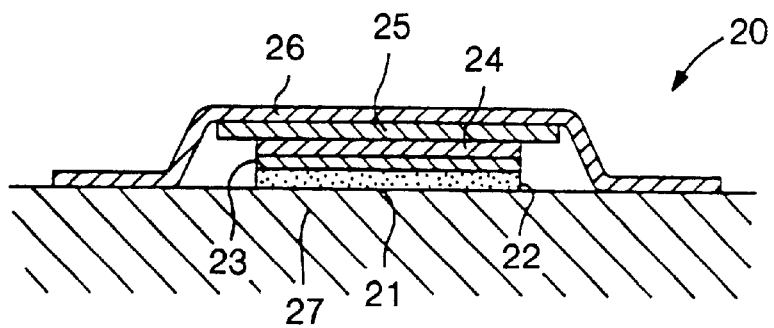
FIG. 3 is a cross-sectional view of yet another embodiment of a transdermal therapeutic drug delivery device which may be used in accordance with this invention.

FIG. 3 illustrates another embodiment of the invention, device 20, shown in placement on the skin 27. In this embodiment, the transdermal drug delivery device 20 comprises multi-laminate drug formulation/enhancer reservoir 21 having at least two zones 22 and 24. Zone 22 consists of a drug reservoir substantially as described with respect to FIG. 2. Zone 24 comprises a permeation enhancer reservoir which is preferably made from substantially the same matrix as is used in zone 22. Zone 24 comprises a permeation enhancer dispersed throughout and is free of any drug in excess of saturation. Rate-controlling membrane 23 for controlling the release rate of the permeation enhancer from zone 24 to zone 22 is placed between the two zones. A rate-controlling membrane (not shown) for controlling the release rate of the enhancer and/or drug from zone 22 to the skin may also optionally be utilized and would be present between the skin 27 and zone 22. Superimposed over the drug formulation/enhancer reservoir 21 of device 20 is an impermeable backing 25 and an adhesive overlay 26. Backing layer 25 is preferably impermeable to the drug and permeation enhancer and is preferably slightly larger than zone 24 in order to prevent the materials in zone 24 from adversely interacting with the adhesive in overlay 26. Other fastening means may be utilized such as an in-line contact adhesive as described above. In addition, a removable liner (not shown) would preferably be provided on the device prior to use and removed prior to application of the device 20 to the skin 27.

The rate controlling membranes may be fabricated from permeable, semi-permeable, or microporous materials which are known in the art to control the rate of drugs into and out of delivery devices or are disclosed in the aforementioned patents previously incorporated herein by reference. Suitable materials include, but are not limited to, polyolefins including polyethylene, polyvinyl acetate and ethylene vinyl acetate copolymers. High density polyethylene and ethylene vinyl acetate copolymers represent preferred rate controlling membrane materials according to the present invention.

Various materials suited for the fabrication of the various layers of the transdermal devices of FIGS. 1–3 are known in the art or are disclosed in the aforementioned patents previously incorporated herein by reference. For example, the matrix making up the drug reservoir/permeation enhancer reservoir of FIGS. 1–3 can be a gel or polymer and may comprise an aqueous or non-aqueous composition. For example, suitable matrix materials include, without limitation, natural and synthetic rubbers or other polymeric material, thickened mineral oil, silicone fluids, polysiloxanes, polyacrylates, ethylene vinyl acetate copolymers, or petroleum jelly.

In addition to any drug and permeation enhancer, the matrix, if needed, may also contain stabilizers, dyes, pigments, inert fillers, tackifiers, excipients and other conventional components of transdermal delivery devices as are known in the art. The transdermal therapeutic devices of the present invention are prepared in a manner known in the art, such as by those procedures, for example, described in the patents listed previously herein.

Figure 4:
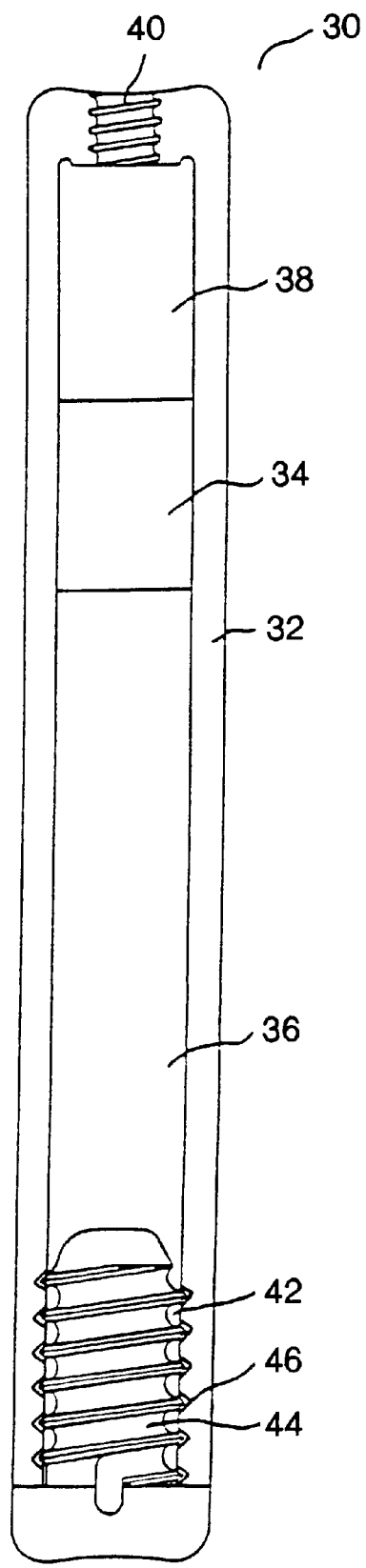
FIG. 4 is a cross-sectional view of one embodiment of a fluid-imbibing drug delivery device which may be used in accordance with the present invention.

Another preferred embodiment, depicted in FIG. 4, is directed to providing membranes for use in diffusional or osmotically driven drug delivery devices such as fluid-imbibing devices described in the patents listed above and in commonly owned copending application Ser. No. 08/791, 699, herein incorporated by reference. These devices can be implanted into an individual to release the drug in a controlled manner for a predetermined administration period. In general, these devices work by imbibing fluid from the outside environment and releasing corresponding amounts of the drug. The volumetric delivery rate of these systems is determined by the design, dimensions, and material properties of the rate controlling membrane and is tightly correlated to the water uptake of the membrane materials. The higher the water uptake of the membrane materials, the higher the water permeation rate through the membrane.

For some membrane materials, for example high water uptake hydrophilic polyurethane, the amorphous domain of the soft segments plays an important role in controlling water uptake, hence water permeation rate, of the membrane. It is expected that after processing, material membrane functionality such as water uptake and water permeation rate may change over time as phase separation occurs. Membrane annealing according to this invention accelerates morphological changes and stabilizes membrane performance, thus providing consistent and predictable membrane functionality. With semi-crystalline materials such as polyurethane, annealing also accelerates the phase separation of hard and soft segments such that crystalline (hard) segments come together to form micro-crystalline regions distributed within the continuous amorphous (soft) non-crystalline region. Membranes annealed according to this embodiment exhibit water uptake and water permeability which are more stable than non-annealed membranes.

After annealing, the membrane is incorporated into a fluid-imbibing device as depicted in FIG. 4. Fluid-imbibing device 30 comprises an impermeable reservoir 32 divided into two chambers by a piston 34. The first chamber 36 is adapted to contain a drug and the second chamber 38 is adapted to contain a fluid-imbibing agent. Preferred fluid-imbibing agents are NaCl with appropriate tableting agents such as povidone, magnesium stearate, sodium carboxy methylcellulose, water, and sodium polyacrylate. Other suitable fluid imbibing agents are the osmagents and osmopolymers described in, for example, U.S. Pat. No. 5,413,572, incorporated by reference herein. Membrane 40 is positioned in sealing relationship with an interior surface of one end of the impermeable reservoir. The membrane can be a sheet-like layer or can be formed into any desired shape by well know procedures such as injection molding, extrusion, and the like. A preferred embodiment comprises a membrane plug as depicted in FIG. 4. In the embodiment depicted in FIG. 4, fluid-imbibing device 30 additionally comprises flow path 42 formed between threaded back-diffusion regulating outlet 44 and threads 46 on the interior surface of reservoir 32.

The membrane 40 controls the rate at which fluid is imbibed into the device and is typically comprised of a polymeric material including, but not limited to, plasticized cellulosic materials, enhanced polymethylmethacrylate such as hydroxyethylmethacrylate (HEMA), and thermoplastic elastomeric materials such as polyurethanes and polyamides, polyether-polyamide copolymers, polyether blocked amides copolymers such as PEBAX®, thermoplastic copolyesters, and the like. Thermoplastic elastomeric materials are preferred as such materials span a wide range of water uptake and water permeability values, are injection moldable and easily processed, swell upon hydration, and are available in durometers widely used for gaskets and seals.

Blended or non-blended polyurethanes are particularly preferred membrane materials. Tecophilic®, a high water uptake, medical grade, aliphatic, polyether polyurethane, manufactured by Thermedics Inc., Woburn Mass., is a particularly preferred membrane material.

Preferred membrane functionality according to this embodiment such as water uptake and water permeability can be obtained by either blending low and high water uptake materials or by direct synthesis of materials of varying water uptake. For example, Tecophilic consists of aliphatic "hard segments" and different proportions of polyethylene glycol (PEG) and polytetramethylene glycol (PTMG) "soft segments", which proportions of PEG and PTMG can be varied during polymer synthesis to provide the desired water uptake and water permeation. Generally, higher water uptake and higher permeability materials comprise a higher proportion of PEG. Various materials for the fabrication of the other components of the fluid-imbibing device of FIG. 4 are known in the art or are disclosed in the aforementioned patents previously incorporated by reference.

Preferred annealing temperatures according to this embodiment are about 50° C.–100° C., preferably about 50° C.–80° C., and most preferably about 55° C.–75° C. The annealing time is about 1–250 hours, preferably about 4–72 hours, and most preferably about 12–48 hours. Prior to annealing, the membranes are stored at room temperature for relaxation, preferably for at least 12 hours–7 days, and more preferably for at least about 2–3 days after processing. The combination of allowing time for membrane relaxation followed by annealing result in the membrane achieving steady-state functionality at a much quicker rate. Membrane annealing according to this embodiment also enhances the mechanical strength of the membrane.

It is believed that this invention has utility in connection with the delivery of a wide variety of drugs. It is to be understood that more than one drug may be delivered by the devices of this invention. For example, suitable drugs for administration by the devices of this invention are disclosed in the aforementioned patents and patent applications previously incorporated by reference. In general, practice of this invention includes devices to be used to deliver therapeutic drugs in all of the major areas, including, but not limited to, ACE inhibitors, adenohypophoseal hormones, adrenergic neuron blocking drugs, adrenocortical steroids, inhibitors of the biosynthesis of adrenocortical steroids, alpha-adrenergic agonists, alpha-adrenergic antagonists, selective alpha-two-adrenergic agonists, analgesics, antipyretics and anti-inflammatory drugs, androgens, local and general anesthetics, antiaddictive drugs, antiandrogens, antiarrhythmic drugs, antiasthmatic drugs, anticholinergic drugs, anticholinesterase drugs, anticoagulants, antidiabetic drugs, antidiarrheal drugs, antidiuretic, antiemetic and prokinetic drugs, antiepileptic drugs, antiestrogens, antifungal drugs, antihypertensive drugs, antimicrobial drugs, antimigraine drugs, antimuscarinic drugs, antineoplastic drugs, antiparasitic drugs, antiparkinson's drugs, antiplatelet drugs, antiprogestins, antithyroid drugs, antitussives, antiviral drugs, atypical antidepressants, azaspirodecanediones, barbituates, benzodiazepines, benzothiadiazides, beta-adrenergic agonists, beta-adrenergic antagonists, selective beta-one-adrenergic antagonists, selective beta-two-adrenergic agonists, bile salts, drugs affecting volume and composition of body fluids, butyrophenones, drugs affecting calcification, calcium channel blockers, cardiovascular drugs, catecholamines and sympathomimetic drugs, cholinergic agonists, cholinesterase reactivators, dermatological drugs, diphenylbutylpiperidines, diuretics, ergot alkaloids, estrogens, ganglionic blocking drugs, ganglionic stimulating drugs, hydantoins, drugs for control of gastric acidity and treatment of peptic ulcers, hematopoietic drugs, histamines, histamine antagonists, 5-hydroxytryptamine antagonists, drugs for the treatment of hyperlipoproteinemia, hypnotics and sedatives, immunosupressive drugs, laxatives, methylxanthines, monoamine oxidase inhibitors, neuromuscular blocking drugs, organic nitrates, opioid analgesics and antagonists, pancreatic enzymes, phenothiazines, LHRH and its analogues such as leuprolide, progestins, prostaglandins, drugs for the treatment of psychiatric disorders, retinoids, sodium channel blockers, drugs for spasticity and acute muscle spasms, succinimides, thioxanthines, thrombolytic drugs, thyroid drugs, tricyclic antidepressants, inhibitors of tubular transport of organic compounds, drugs affecting uterine motility, vasodilators, vitamins and the like.

The following examples are offered to illustrate the practice of the present invention and are not intended to limit the invention in any manner.

EXAMPLE 1

Transdermal therapeutic systems comprising an aqueous ethanolic gel were prepared according to the following procedure. Fentanyl base was added to a mixture of 95% ethanol and purified water. 2% of hydroxyethyl cellulose gelling agent was added slowly to the solution with stirring and mixed until a smooth gel was obtained (approximately 1 hour). A 0.05 mm thick contact adhesive layer was formed on a release liner for the system by solution casting an amine resistant silicone medical adhesive (XCF 2992, Dow Corning, Midland Mich.) onto the polyester film from a solution in heptane.

An annealed or non-annealed rate controlling membrane comprised of EVA (9% VA) was pressure laminated to the exposed adhesive as set forth in the system configuration shown in Table 1 below. The rate controlling membranes subjected to an annealing process according to this invention (systems 2 and 4) were maintained at about 60° C. for a period of time of about 24 hours and subsequently allowed to cool to ambient conditions for 2 days before being pressure laminated to the adhesive.

TABLE 1

| SYSTEM CONFIGURATION | | |
|---|---|---|
| SYSTEM (symbol in Fig. 7) | MEMBRANE ANNEALING | MEMBRANE THICKNESS (mil) |
| 1 (*) | NO | 2.0 |
| 2 (□) | YES | 3.0 |
| 3 (■) | NO | 3.5 |
| 4 (Δ) | YES | 2.0 |
| 5 (▲) | NO | 2.0 |

A backing member comprised of a multilaminate of polyester thylene, aluminum, polyester and EVA (Scotchpak 1220, 3M Co., St. Paul, Minn.) was also provided and the aqueous gel was pouched between the backing member and the release liner/adhesive/rate controlling membrane on a rotary heat-seal machine. Sealed pouches in sizes of 5 cm² were die cut and immediately pouched to avoid loss of ethanol. The pouched systems were allowed to equilibrate for at least two weeks in order to reach equilibrium concentration of the drug and ethanol in the rate controlling and adhesive layers.

The peelable liner of the laminate was removed and the fentanyl releasing surface was placed against the stratum corneum side of a disc of human epidermis which had been blotted dry just prior to use. The excess epidermis was wrapped around the device so that none of the device edge was exposed to the receptor solution. The device covered with epidermis was then mounted on a Teflon® holder of a release rate rod using nylon mesh and metal string. The rod was then reciprocated in a fixed volume of receptor solution (0.05M phosphate buffer, pH 6.5) at 35° C.

At given time intervals, the entire receptor solution was removed from the test tubes and replaced with an equal volume of fresh receptor solutions previously equilibrated at 35° C. The receptor solutions were stored in capped vials at 4° C. until assayed for fentanyl base or ethanol content by HPLC analysis. From the drug concentration and the volume of the receptor solutions, the area of permeation and the time interval, the flux of the drug was calculated as follows: (drug concentration×volume of receptor)/(area×time)=flux ($\mu$g/cm$^2$·hr).

Figure 7:
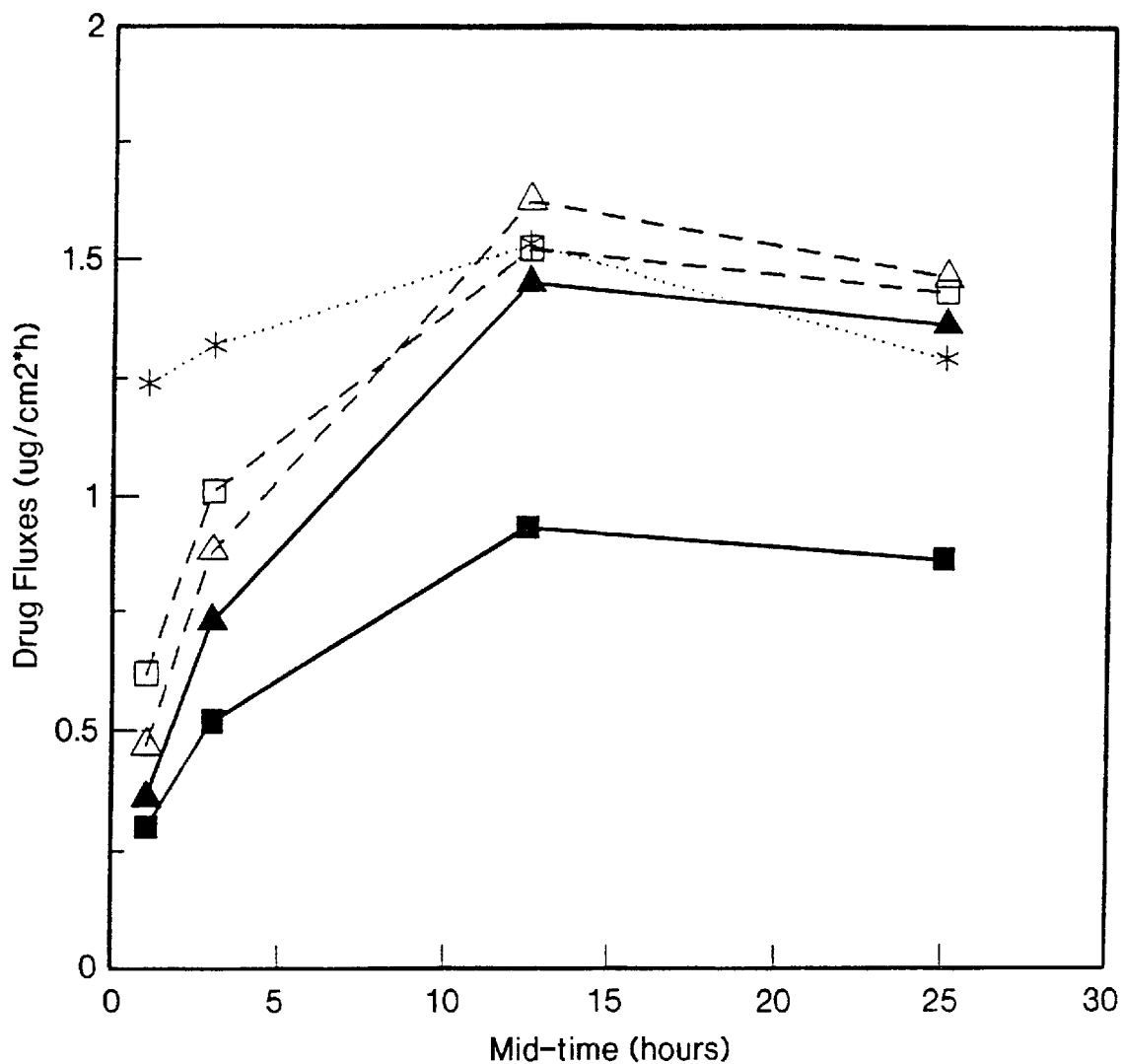
FIG. 7 is a plot of the in vitro skin flux of fentanyl from systems according to this invention with annealed and non-annealed rate controlling membranes.

FIG. 7 depicts the in vitro flux of fentanyl through skin from the systems prepared as set forth above. As seen in FIG. 7, the systems comprising the annealed rate controlling membranes demonstrated a higher flux of fentanyl therethrough as compared to the non-annealed systems. There was significantly less variation of drug fluxes between the systems comprising the annealed membranes as compared to the variation in fluxes observed among the systems comprising non-annealed membranes.

Figure 8:
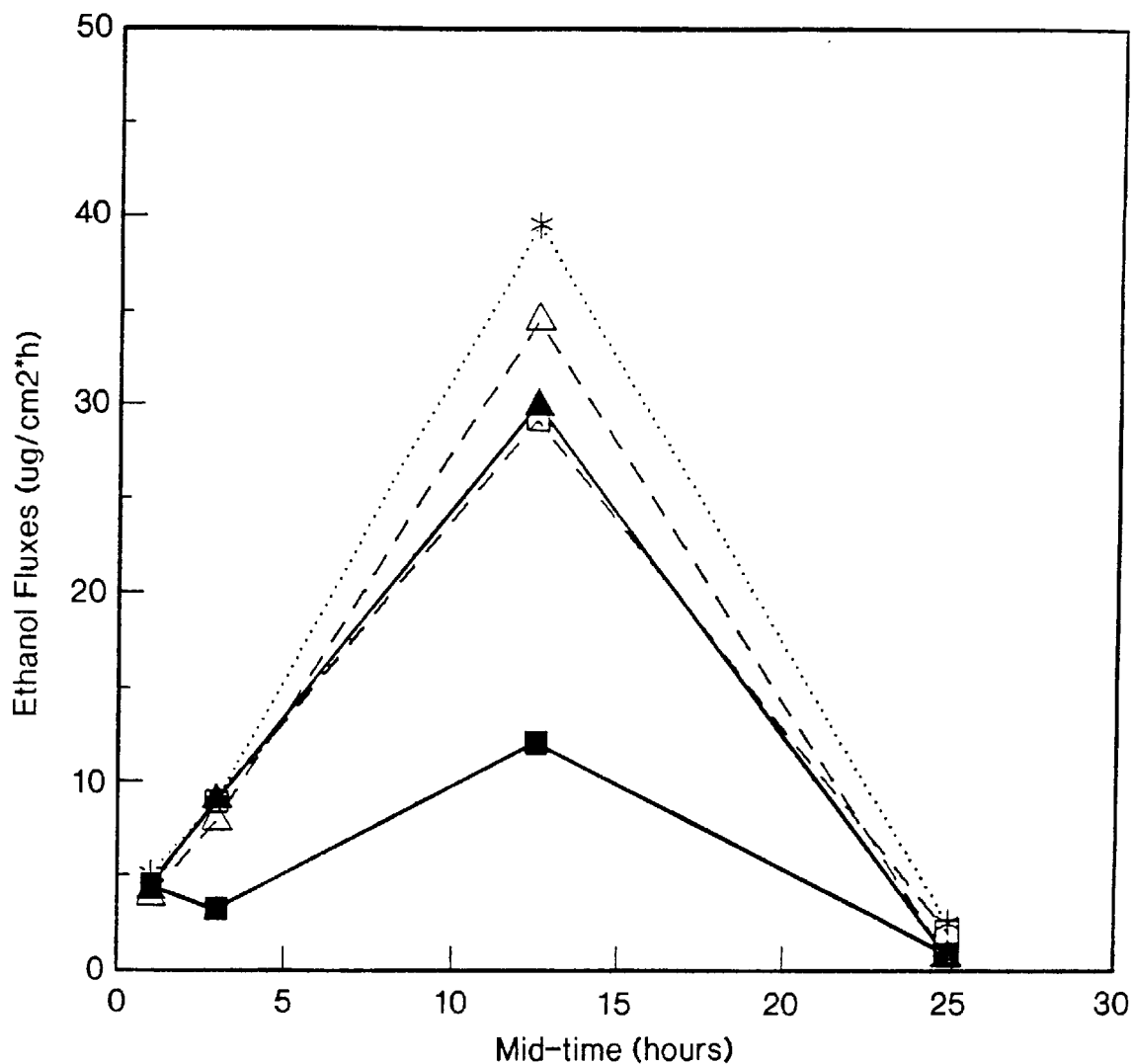
FIG. 8 is a plot of the in vitro skin flux of ethanol from systems according to this invention with annealed and non-annealed rate controlling membranes.

FIG. 8 depicts the in vitro flux of ethanol through skin from the systems prepared as set forth above. As seen in FIG. 8, the systems comprising the annealed rate controlling membranes demonstrated a more consistent, higher flux of ethanol therethrough as compared to the systems with non-annealed membranes.

EXAMPLE 2

Systems comprising 2 mil, 3 mil, or 3.5 mil EVA (9% VA) membranes and a surface area of 10 cm$^2$ were prepared according to the procedure set forth in Example 1. The 2.0 mil EVA membranes in roll form were annealed in a sauna room at 60° C. for 2–34 hours, while the 3.0 and 3.5 mil EVA membranes were annealed in an oven at 60° C. for two hours. The release rates of fentanyl and ethanol from systems comprising annealed membranes were then measured and compared to release rates measured from control systems comprising non-annealed membranes.

Release rates were measured by placing the systems in closed jars containing a fixed amount of a receptor solution (0.05M phosphate buffer, pH 6.5) at 35° C. At given time intervals, the entire receptor solution was removed from the jars and replaced with an equal volume of fresh receptor solutions previously equilibrated at 35° C. The receptor solutions were stored in capped vials at 4° C. until assayed for fentanyl base or ethanol content by HPLC analysis. From the drug concentration and the volume of the receptor solutions, the area of permeation and the time interval, the flux of the drug was calculated as follows: (drug concentration×volume of receptor)/(area×time)=flux ($\mu$g/cm$^2$·hr). The average in vitro release rate of fentanyl and ethanol are shown in Table 2.

TABLE 2

Average Release Rates of Fentanyl and Ethanol from Annealed vs. Non-annealed Systems

| MEMBRANE | FENTANYL RELEASE RATE ($\mu$g/cm$^2$ · hr) | ETHANOL RELEASE RATE ($\mu$g/cm$^2$ · hr) |
|---|---|---|
| 2 mil control | 3.6 | 35 |
| 2 mil annealed | 4.6 | 47 |
| 3 mil control | 3.3 | 20 |
| 3 mil annealed | 4.0 | 39 |
| 3.5 mil control | 3.2 | 29 |
| 3.5 mil annealed | 4.6 | 35 |

EXAMPLE 3

Figure 9:
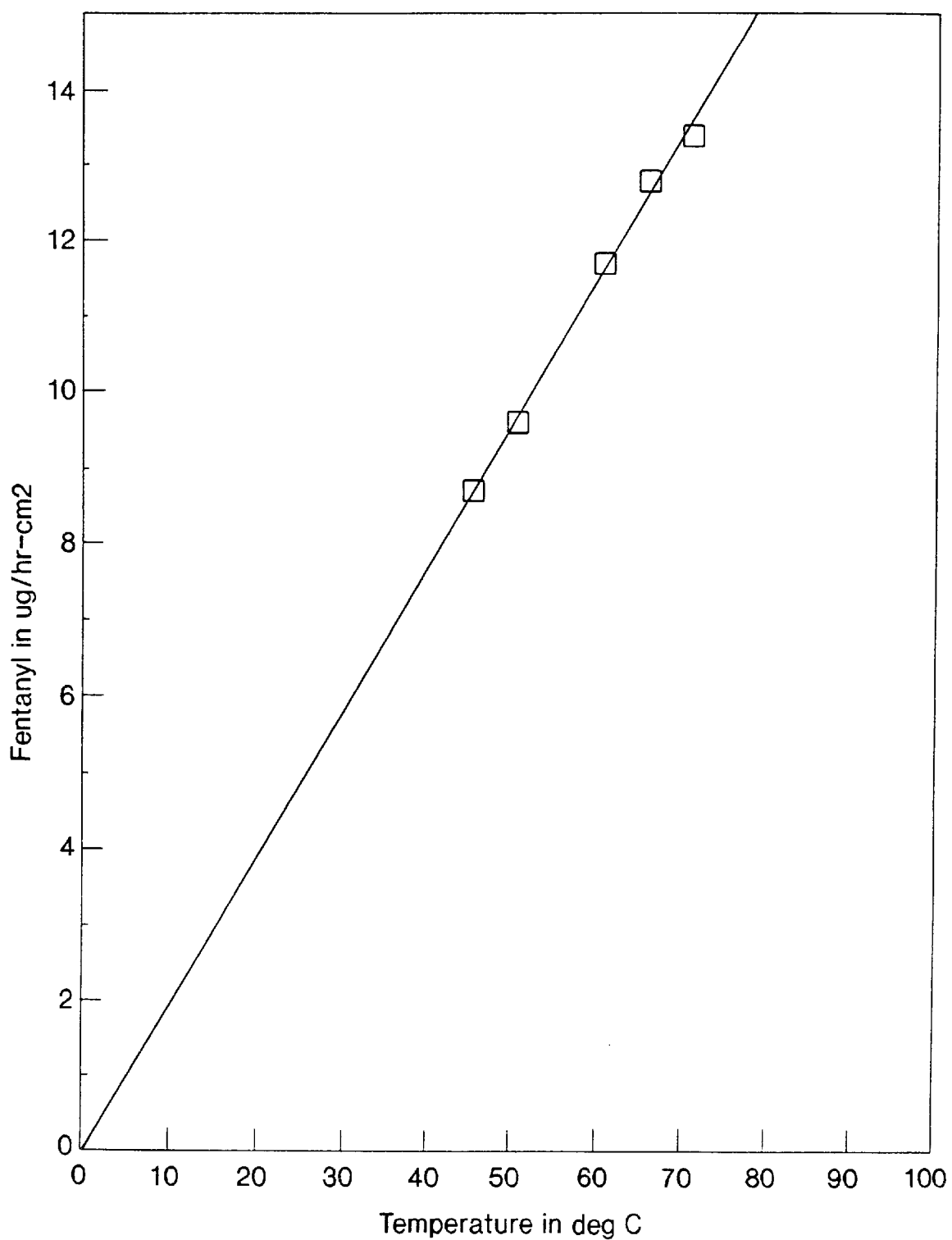
FIG. 9 is a plot of the in vitro skin flux of fentanyl vs. the annealing temperature.

The effect of annealing temperature on fentanyl flux was studied. Systems were made according to the procedure set forth in Example 1. The rate controlling membranes were annealed at various temperatures ranging from 45–80° C. for two hours. The flux of fentanyl from these systems was then measured by the skin flux experiments described in Example 1. The results are shown in FIG. 9, which is a plot of the average fentanyl flux ($\mu$g/cm$^2$·hr) over the period 2–29 hours following application of the system vs. temperature of the annealing process. As seen in FIG. 9, the average flux of fentanyl during the 2–29 hour period increased substantially linearly with increasing annealing temperature.

EXAMPLE 4

The effect of storage on the permeability stability of an EVA membrane was investigated. Donor solutions were prepared by adding fentanyl base to a mixture of 95% ethanol and purified water. 2% of hydroxyethyl cellulose gelling agent was added slowly to the solution with stirring and mixed until a smooth gel was obtained (approximately 1 hour). Flux experiments were performed to measure the flux of fentanyl from the donor solution through annealed EVA film containing 9% vinyl acetate (EVA 9) and compared to fentanyl flux through a non-annealed EVA 9 membrane. The EVA 9 membranes were annealed at 60° C. for 2 hours. Membrane 1 was annealed 15 months prior to the flux experiment while membrane 2 was annealed on the day of the flux experiment.

The experiment was carried out using standard glass diffusion cells which consist of a donor compartment and a receptor compartment. The rate controlling membrane was placed in each diffusion cell in a horizontal position between a lower capped receptor compartment and an upper capped donor compartment. The receptor compartment has both a venting tube (uncapped) and a sampling port (capped). An O-ring was positioned between the membrane and the donor compartment, and a clamp held the compartments together. The receptor solution, 0.05M phosphate buffer, pH 6.5, was added to each receptor compartment. The cells were placed in a temperature controlled water bath shaker at 35° C. and allowed to come to temperature before the donor solution was added. The donor solution comprised fentanyl gel with a large excess of fentanyl in order to maintain constant steady state flux throughout the 30 hour sampling period.

At each time interval, the receptor solution was removed from the test cell and replaced with an equal volume of fresh receptor solution previously equilibrated at 35° C. The receptor solutions for each time interval were then assayed for fentanyl by HPLC analysis to calculate the permeation rate of fentanyl through the membrane from the donor solutions. From the drug concentration and the volume of the receptor solutions, the area of permeation and the time interval, the flux of the drug through the rate controlling membranes was calculated as follows: (drug concentration× volume of receptor)/(area×time)=flux ($\mu g/cm^2 \cdot hr$).

TABLE 3

Effect of Storage on EVA 9 Membrane Permeability

| MEMBRANE | ANNEALLING | FENTANYL FLUX ($\mu g/cm^2 \cdot hr$) |
|---|---|---|
| membrane 1 | 60° C. for 2 hours | 11.0 |
| membrane 2 | 60° C. for 2 hours | 10.8 |
| membrane 3 | none | 6.5 |

As seen in Table 3, the permeability of membrane 1 was stable after 15 months storage at room temperature.

EXAMPLE 5

Tests were done to study the effects of annealing on high density polyethylene (HDPE) films using nicotine as a model drug. Drug reservoirs were prepared by mixing 60 wt % ethylene vinyl acetate (39% vinyl acetate) and 40 wt % nicotine base and were allowed to equilibrate to room temperature. 10 cm² patches were prepared by placing approximately 0.4 grams of the drug reservoir on the heat sealable (silver side) of a Scotchpak polyester backing using a syringe. HDPE resins (LR723, LR734 and LS901, Millenium, Texas) were cast into films which were then heated in an oven at 70° C. for a period of two hours. An HDPE film to be tested was placed over the drug reservoir mixture, and a piece of Teflon film was placed over the HDPE film and the films were heat sealed together. Finished systems were cut from the prepared laminate by hand punching around the heat sealed zone.

In vitro release rate experiments were performed to measure the release of nicotine through annealed HDPE film and compared to nicotine release through a non-annealed HDPE membrane. The release liner was removed and the device was then mounted on a Teflon® holder of a release rate rod using Nylon mesh and metal wire. The rod was then reciprocated in a fixed volume of receptor solution (distilled water) at 32° C.

At given time intervals, the entire receptor solution was removed from the test tubes and replaced with an equal volume of fresh receptor solutions previously equilibrated at 32° C. The nicotine concentration in the distilled water receptor was measured by UV absorption at 260 nm. From the drug concentration and the volume of the receptor solutions, the area of permeation and the time interval, the flux of the drug was calculated as follows: (drug concentration×volume of receptor)/(area×time)=flux ($\mu g/cm^2 \cdot hr$). The results are shown in Table 4.

TABLE 4

Nicotine Flux ($\mu g/cm^2 \cdot hr$) Through Annealed and Non-Annealed HDPE Films

| HDPE Resin | Film Treatment | Thickness (mil) | Nicotine Flux |
|---|---|---|---|
| LP 5102 | Non-annealed | 1.90 | 31.47 |
| LP 5102 | Annealed | 1.90 | 44.13 |
| LR 723 | Non-annealed | 2.40 | 20.67 |
| LR 723 | Annealed | 2.40 | 26.19 |
| LR 734 | Non-annealed | 2.13 | 11.41 |
| LR 734 | Annealed | 2.13 | 15.15 |
| LS 901 | Non-annealed | 1.23 | 19.09 |
| LS 901 | Annealed | 1.23 | 22.78 |

As seen from Table 4, the systems comprising annealed membranes resulted in a greater flux of nicotine than systems comprising non-annealed rate controlling membranes.

EXAMPLE 6

The effect of the vinyl acetate content on the permeability of EVA rate controlling membranes using testosterone as the model drug was investigated. A reservoir gel comprising 26 wt. % testosterone, 1–2 wt. % hydroxypropyl cellulose, and the remainder 95% ethanol was prepared by mixing testosterone, 95% ethanol and adding hydroxypropyl cellulose with mixing.

A contact adhesive composition was made by mixing polyisobutylene (MW 1,200,000), polyisobutylene (MW 35000) and light mineral oil. A 50 micron thick layer of the contact adhesive was cast onto a 75 micron thick film of siliconized polyethylene terephthalate peelable liner. The contact adhesive side of the resulting two layer subassembly was laminated to a 50 micron thick film of annealed or non-annealed ethylene vinyl acetate (EVA) copolymer of various vinyl acetate content as set forth in Table 5. The annealed EVA membranes were heated at 42° C. for 5 days. The gelled testosterone-ethanol mixture was placed on the EVA membrane. A backing member comprised of aluminized polyethylene terephthalate with an EVA heat sealable coating was laid over the gels and heat-sealed to the EVA copolymer using a rotary heat seal machine, Finished systems were die-cut from laminate using a circular punch and placed in sealed pouches to prevent loss of volatile components.

The peelable liner of the laminate was removed and the system was then mounted on a Teflon® rod. A known volume of receptor solution (0.10% phenol/$H_2O$) was then placed in a test tube and was equilibrated at 35° C. The Teflon rod with the attached system was then placed in a water bath at 35° C. Mixing was accomplished by attachment to a motor which caused constant vertical mixing.

At given time intervals, the entire receptor solution was removed from the test tubes and replaced with an equal volume of fresh receptor solutions previously equilibrated at 35° C. The receptor solutions were stored in capped vials at 40° C. until assayed for testosterone content by HPLC analysis. From the drug concentration and the volume of the receptor solutions, the area of permeation and the time interval, the flux of the drug was calculated as follows: (drug concentration×volume of receptor)/(area×time)=flux ($\mu g/cm^2 \cdot hr$).

TABLE 5

Average Release Rate of Testosterone Through
Annealed and Non-Annealed EVA Membranes of Varying VA Content

| % Vinyl Acetate (VA) | AVG (12–30 hr) Testosterone release rate through non-annealed membrane ($\mu g/cm^2 \cdot hr$) | AVG (12–30 hr) Testosterone release rate through annealed membrane ($\mu g/cm^2 \cdot hr$) |
|---|---|---|
| 12.2 | 1.39 | 1.56 |
| 9 | 1.04 | 1.22 |
| 9 | 1.02 | 1.21 |
| 6.6 | 0.46 | 0.50 |

EXAMPLE 7

10 cm² systems containing fentanyl were prepared as set forth in Example 1. EVA membranes (thickness of 50 micron) comprising 6.6% VA were compared to systems comprising 9% VA. The systems were exposed to various thermal stresses prior to conducting in vitro release rate studies following the procedure set forth in Example 1 to determine if membrane permeability exceeded a preferred maximum limit after thermal stressing. The preferred maximum release from the system is less than 34.5 $\mu g/cm^2 \cdot hr$ for the period 0–2 hours after application, less than 6.8 $\mu g/cm^2 \cdot hr$ for the period 2–12 hours after application, and less than 4.7 $\mu g/cm^2 \cdot hr$ for the period 12–24 hours after application. As seen in Table 6, the annealed EVA 9 membrane exceeded the predetermined limits for the 0–2 and 2–12 hr intervals while the annealed EVA 6.6 membrane was within these limits after thermal stressing at 50° C. for one day.

TABLE 6

Release Rate of Fentanyl After Heat Stressing

| % VA | Heat Stress | 0–2 hr release ($\mu g/cm^2 \cdot hr$) | 2–12 hr release ($\mu g/cm^2 \cdot hr$) | 12–24 hr release ($\mu g/cm^2 \cdot hr$) |
|---|---|---|---|---|
| 6.6 | none | 6.1 | 1.8 | 1.45 |
| 9 | none | 12.9 | 3.6 | 2.76 |
| 6.6 annealed | none | 7.5 | 3.49 | 2.78 |
| 6.6 annealed | 45° C., 16 hrs | 27.4 | 6.4 | 3.8 |
| 6.6 annealed | 45° C., 40 hrs | 27.8 | 6.3 | 3.95 |
| 6.6 annealed | 50° C., 4 hrs | 22.1 | 5.75 | 3.85 |
| 6.6 annealed | 50° C., 16 hrs | 24.8 | 6.4 | 4.0 |
| 6.6 annealed | 50° C., 24 hrs | 27.3 | 6.26 | 3.59 |
| 9 annealed | 50° C., 24 hrs | 41.0 | 8.9 | 3.6 |

EXAMPLE 8

Figure 10:
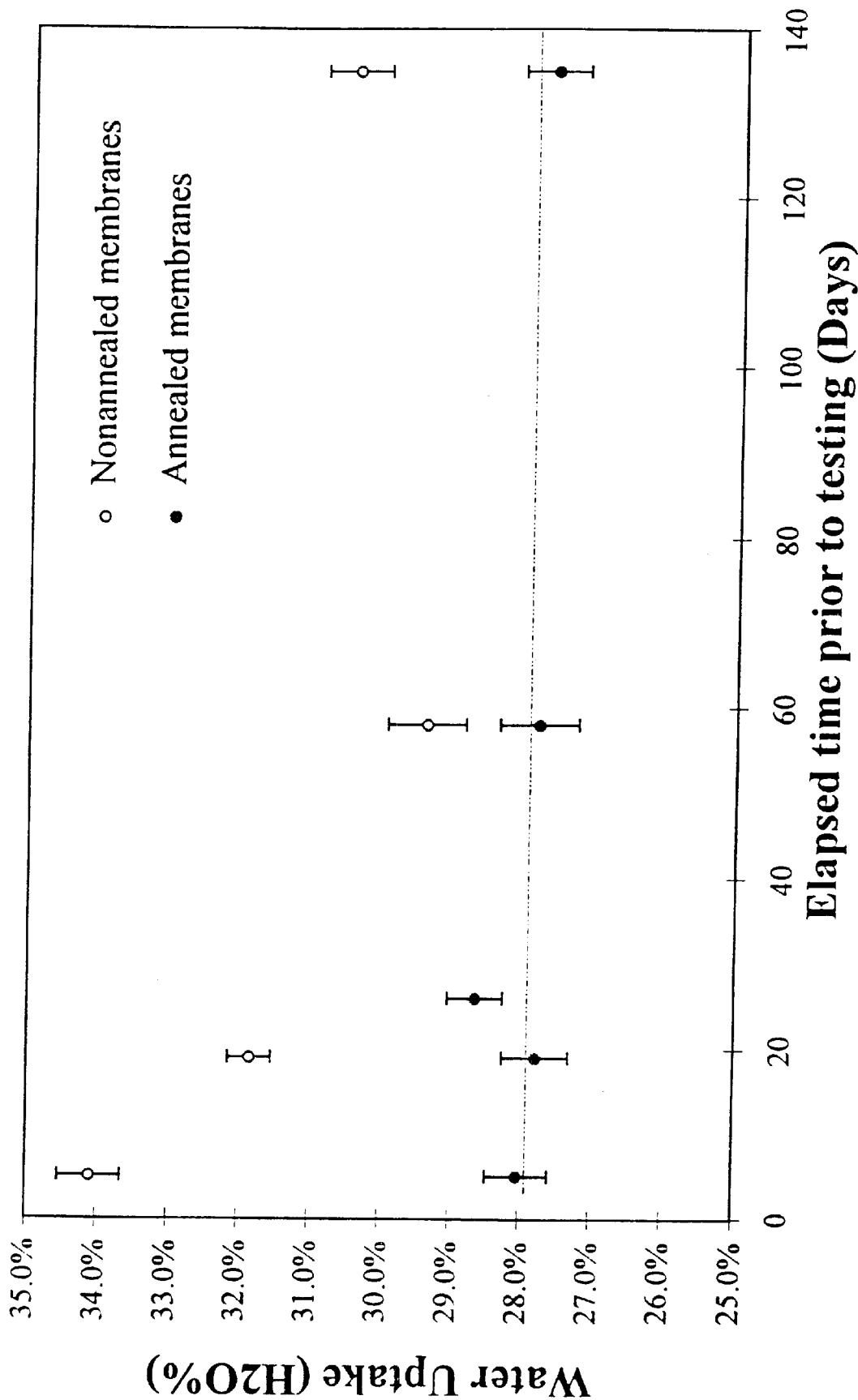
FIG. 10 is a plot depicting water uptake of annealed and non-annealed polyurethane membranes.
Figure 11:
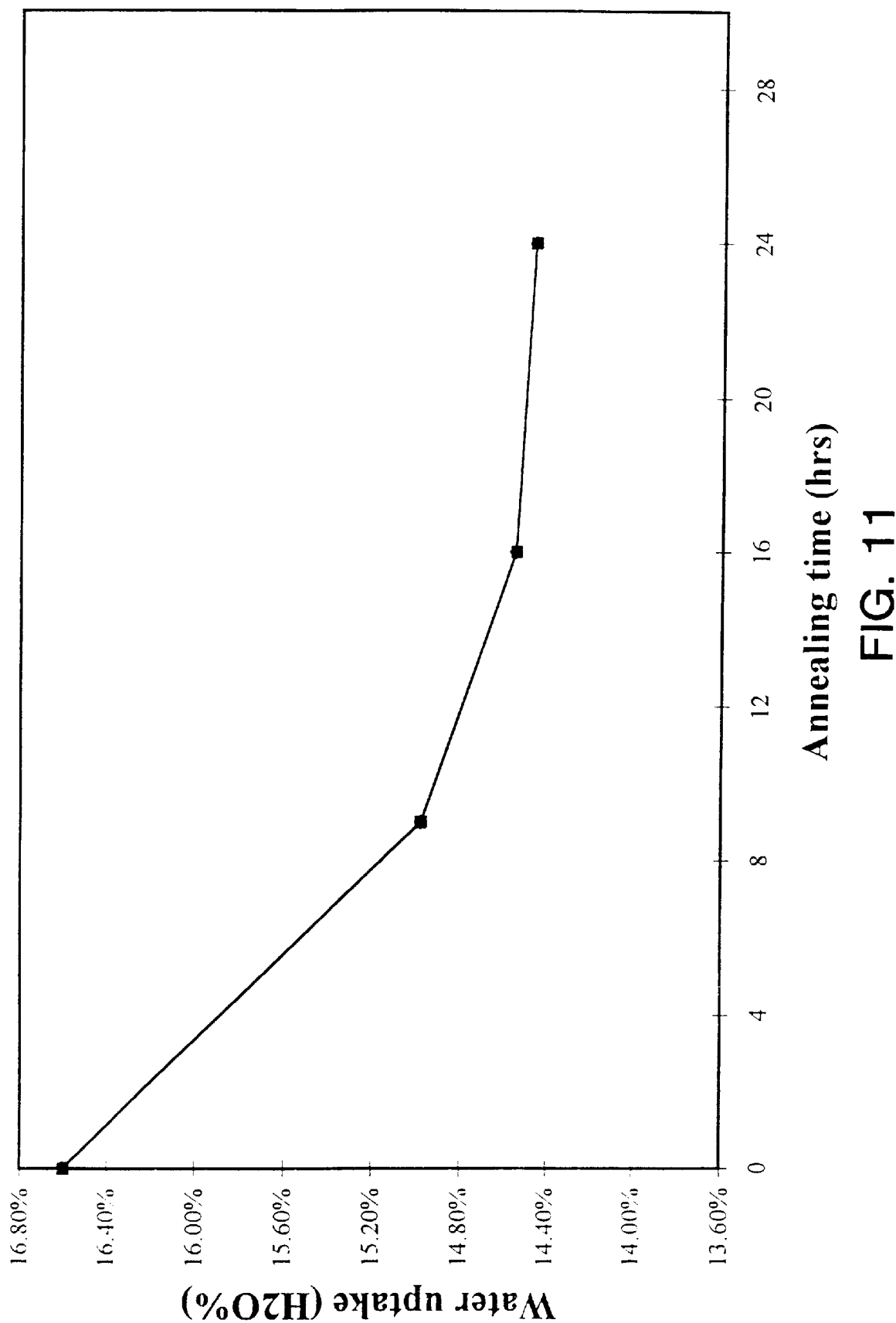
FIG. 11 is a plot depicting water uptake vs. annealing time of polyurethane plug membranes.

Tests were performed to observe annealing effects on water uptake of polyurethane membranes. Polyurethane membranes (blend of 65% Tecophilic® HP-60D-35 and 35% Tecoflex® EG-85A, Thermedics, Inc.) were heated at 52° C. for 0, 4, 8, 16, 24, and 32 hours and thereafter weighed and stored in sealed bags at room temperature. The membranes were then placed in 15 ml of water at 37° C. for 7 days, removed, and blotted dry to remove any surface water prior to weighing. Water uptake was calculated as: Water uptake $(H_2O\%)=(W_w/W_d) \times 100$ where $W_w$ is the membrane weight after being removed from water and $W_d$ is the dry membrane weight after the heat treatment. FIG. 10 shows the water uptake of annealed and non-annealed membranes as a function of time prior to testing. As seen in FIG. 10, the annealed membranes exhibited much more consistent water uptake values compared to non-annealed membranes. FIG. 11 shows the water uptake as function of annealing time.

EXAMPLE 9

Figure 12:
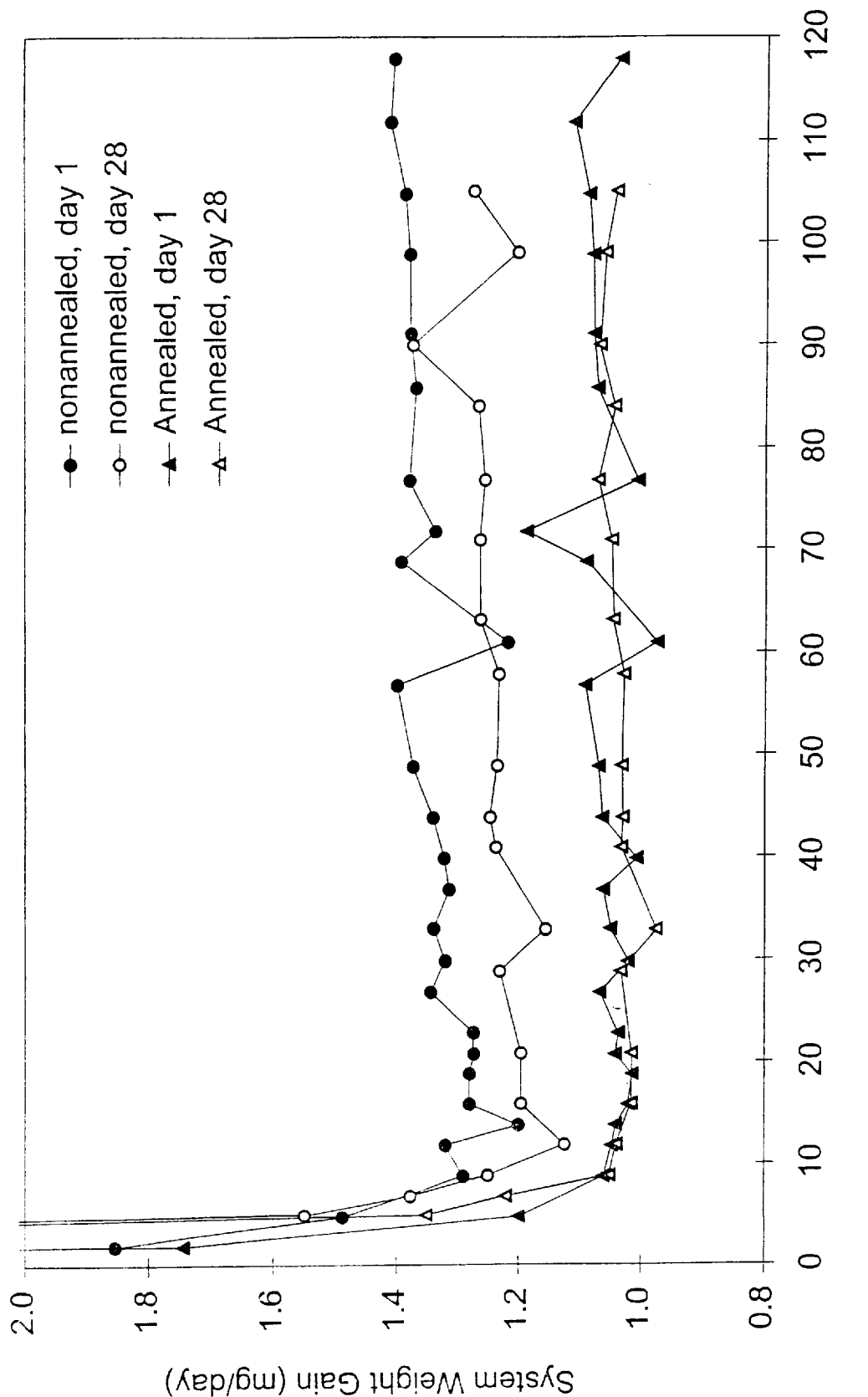
FIG. 12 is a plot depicting system weight gain vs. time for systems comprising annealed and non-annealed membranes.

Tests were performed to observe annealing effects on water permeability of polyurethane membranes by measuring the weight gain of devices depicted in FIG. 4 incorporating annealed and non-annealed membranes. Two sets of polyurethane membrane plugs (Tecophilic® HP-60D-35, Thermedics, Inc.) were formed by injection molding. One set was annealed at 65° C. for 24 hours and the other set was not subjected to annealing. One half of each set of the membranes were immediately fabricated into systems for weight gain testing (day 1) and the other half were stored for 28 days at which time systems were fabricated and tested for weight gain. The piston 34 and reservoir 32 were lightly lubricated with silicone medical fluid. The piston 34 was then inserted into the open end of chamber 36. Membrane plug 40 was then inserted by lining up the plug with the reservoir and gently pushing the plug until it was fully engaged in the reservoir. The system was then placed in a test medium (37° C. deionized water) and the weight of the system was measured gravimetrically as a function of time. In order to prevent water from seeping into the formulation chamber through the orifice, the system was inserted into a form-fitting hole cut into the lid of a vacutainer such that the membrane end is enclosed in the vacutainer and the orifice end protrudes out of the container. The vacutainer was then filled with test medium which surrounded the membrane end of the system. The entire assembly was placed in a secondary vial which was sealed and placed in a 37° C. water bath. System weight gain was measured by removing the system from the vacutainer, wiping it dry, weighing it, and then returning the system to the water bath filled vacutainer which was then replaced in the heated water bath. The weight gain rate is calculated as $\Delta W/\Delta t=[W_{(i)}-W_{(i-1)}]/[t_{(i)}-t_{(i-1)}]$ where $W_{(i)}$ is the system weight at time $t_{(i)}$. The results are depicted in FIG. 12.

EXAMPLE 10

Release rates from systems comprising annealed and non-annealed membranes were compared. Membranes were prepared and placed in systems according to Example 9. Half of each set of the membranes were immediately fabricated into systems and tested for release rate (day 1) and the other half were stored for 28 days at which time systems were fabricated and tested for release rate. The systems were filled with a blue dye solution consisting of 1–2% blue dye in 98–99% water. Testing was performed by placing dye filled systems in glass test-tubes filled with pre-warmed liquid (35 ml of distilled water or phosphate buffered saline solution). Periodic sampling was performed over 130 days by transferring the systems into fresh pre-filled, pre-warmed test-tubes and measuring the amount of dye in the old test-tubes.

Figure 13:
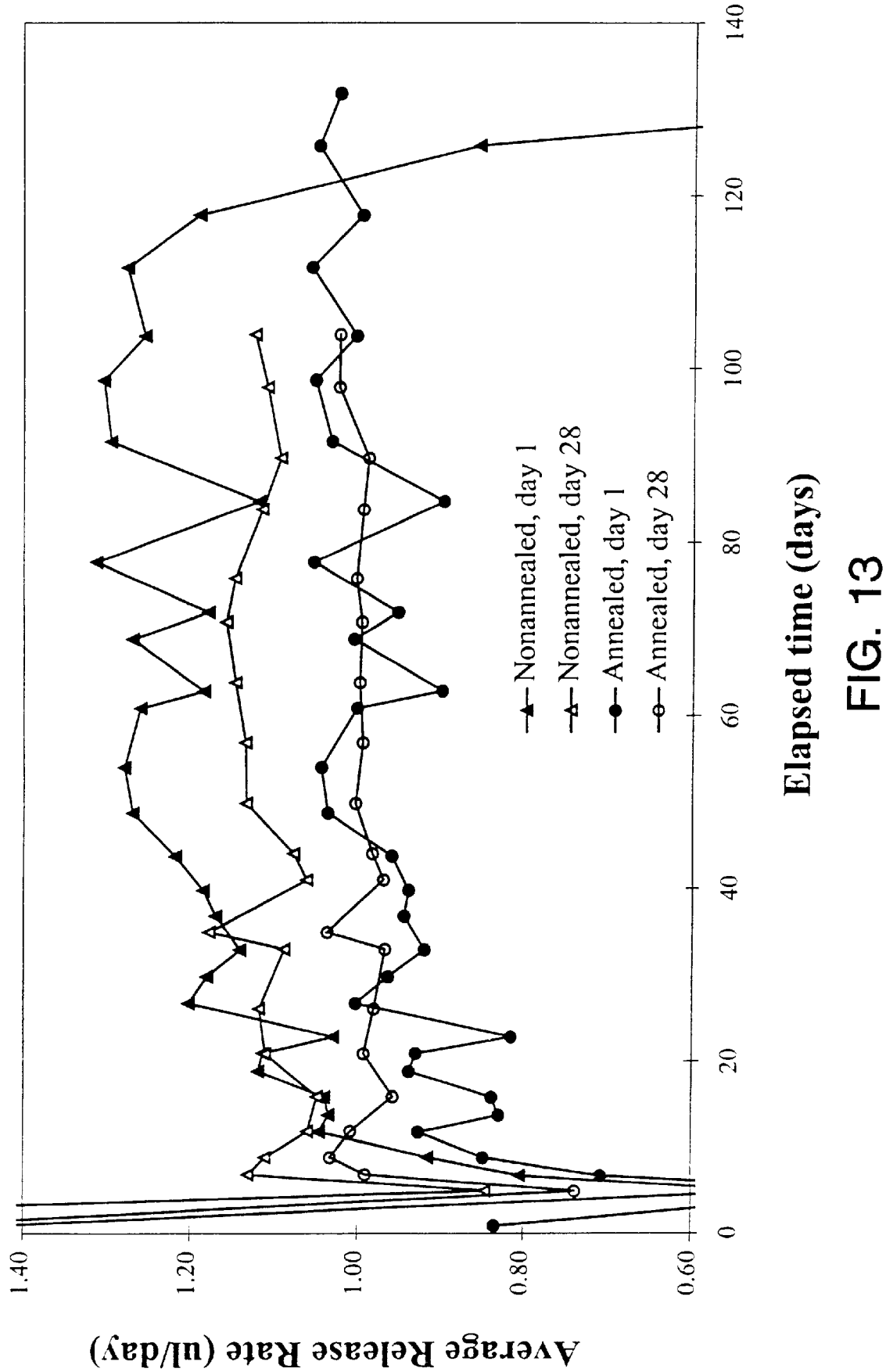
FIG. 13 is a plot depicting average system release rate vs. time from systems comprising annealed and non-annealed membranes.

The release rate was determined by measuring the absorbance of the surrounding release media using a spectrophotometer. Standard setting for blue dye is 630 nm and a standard curve for all formulations was prepared. Release rate (µl/day) was determined by comparing the absorbance of release media to the standard curve. The results are depicted in FIG. 13.

EXAMPLE 11

Figure 14:
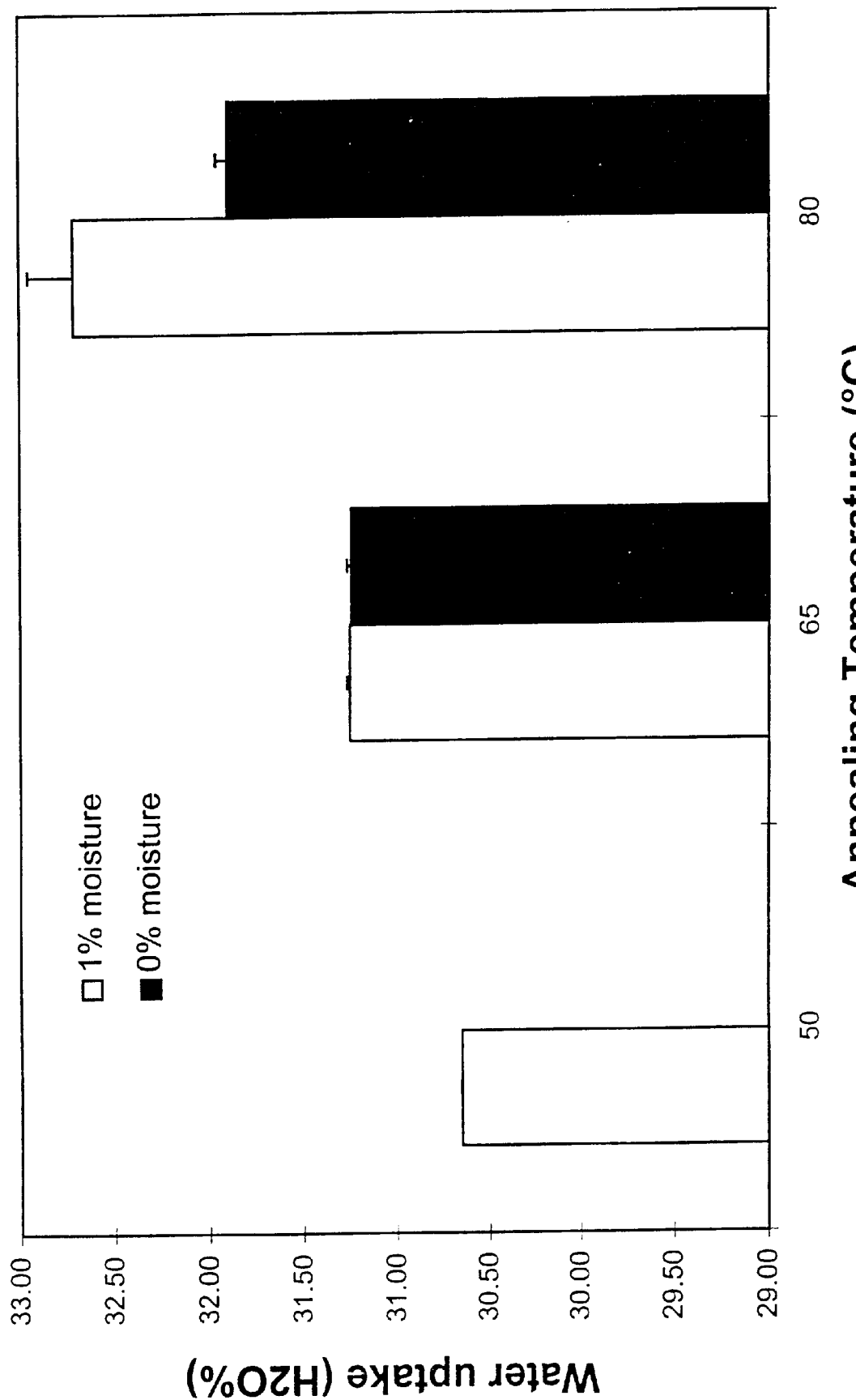
FIGS. 14 and 15 are plots depicting water uptake vs. annealing temperature for various polyurethane membranes at dry or 1% moisture conditions in the annealing oven.
Figure 15:
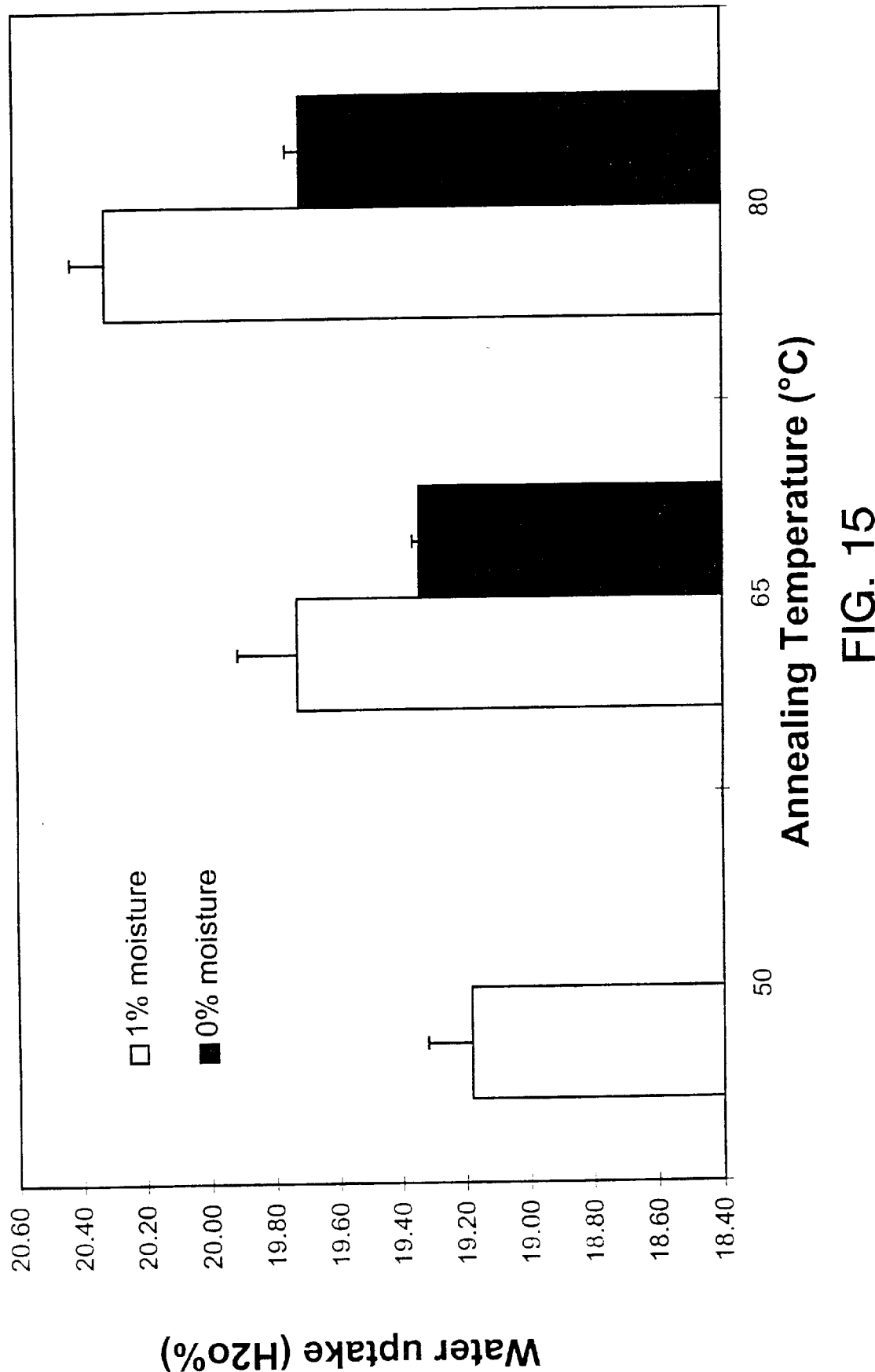
Figure 16:
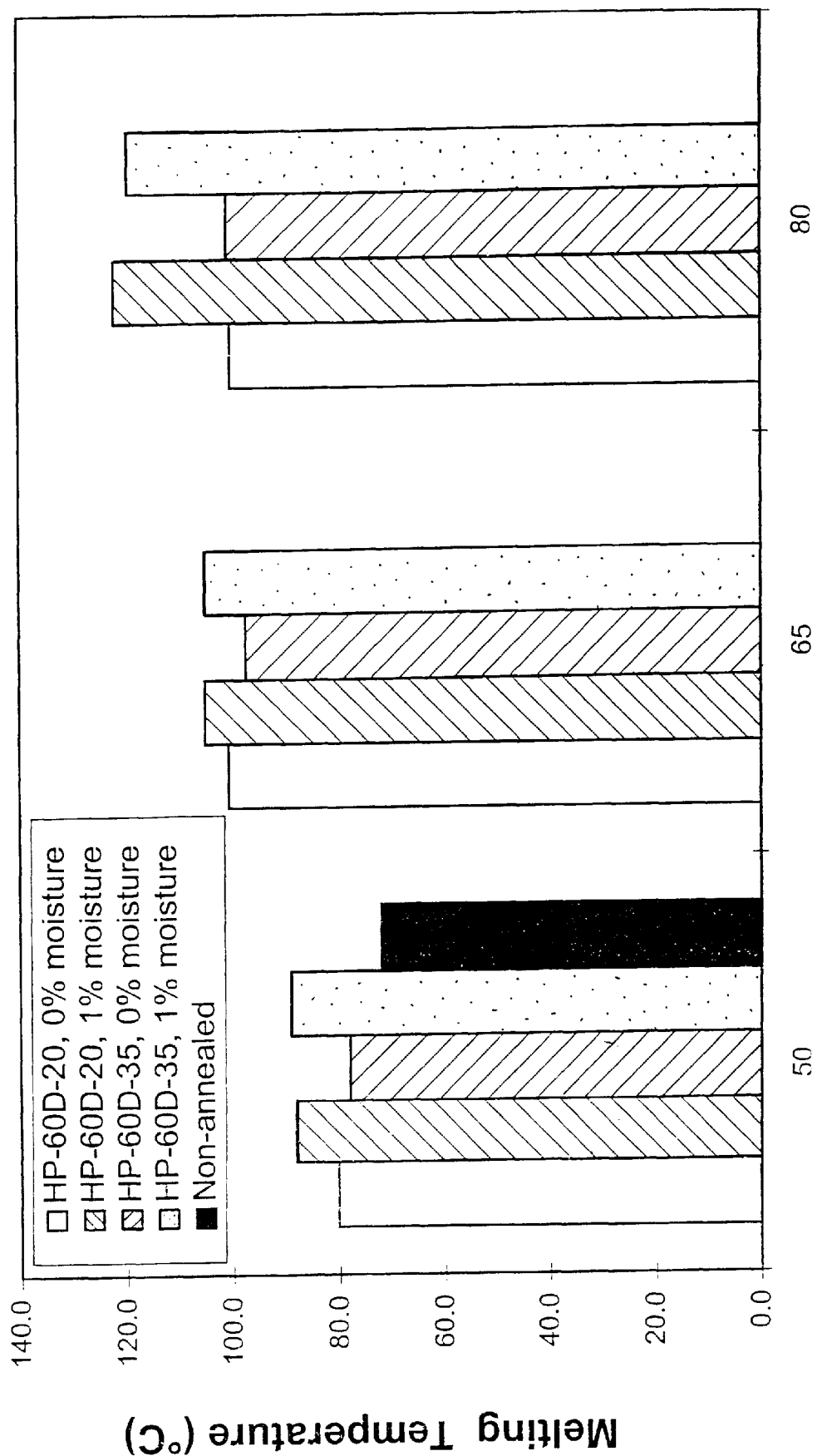
FIG. 16 is a plot depicting the effect of annealing temperature and moisture content on the melt temperature of the hard segment of polyurethane.

The effect of annealing temperature and moisture content on water uptake of annealed membrane plugs was investigated. Polyurethane (HP-60D-35, HP-60D-20, Thermedics, Inc.) membrane plugs were formed by injection molding. The membrane plugs were then annealed for 24 hours at 50° C., 65° C., or 80° C. at moisture conditions of 0 or 1%. Water uptake was determined by the procedure set forth in Example 8. FIG. 14 depicts the results for the HP-60D-35 membranes and FIG. 15 depicts the results for the HP-60D-20 membranes. FIG. 16 shows the effect on the melting temperature of the hard segment of polyurethane at these annealing temperatures and moisture conditions.

Having thus generally described our invention and described certain specific embodiments thereof, including the embodiments that applicants consider the best mode of practicing their invention, it should be readily apparent that various modifications to the invention may be made by workers skilled in the art without departing from the scope of this invention which is limited only by the following claims.

What is claimed is:

1. A rate controlling membrane for a controlled drug delivery device characterized by being subjected to an elevated temperature of about 30° C. to about 5° C. below the melting temperature of the membrane polymer for a predetermined period of about 1–250 hours prior to combination with adnig containing component of said delivery device.

2. A rate controlling membrane according to claim 1 wherein the membrane material is selected from the group consisting of ethylene vinyl acetate copolymers, polyethylene, ethylene copolymers, ethylene oxide copolymers, polyamides, cellulosic materials, polyurethanes, polyether blocked amides copolymers, and polyvinyl acetate.

3. A rate controlling membrane according to claim 1 wherein the membrane comprises ethylene vinyl acetate copolymer.

4. A rate controlling membrane according to claim 3 wherein the vinyl acetate content is about 4–18%.

5. A rate controlling membrane according to claim 4 wherein the membrane is characterized by a DSC profile having a primary peak at about 94–99° C. and a secondary peak at greater than about 50° C.

6. A rate controlling membrane according to claim 5 wherein the vinyl acetate content is about 5–12%.

7. A rate controlling membrane according to claim 2 or 5 wherein the device is a transdermal drug delivery device comprising a drug reservoir layer between a backing layer and a contact adhesive layer, said rate controlling membrane is on the skin-proximal side of the drug reservoir layer.

8. A rate controlling membrane according to claim 7 wherein the drug reservoir comprises a drug selected from the group consisting of testosterone, estradiol, and fentanyl.

9. A rate controlling membrane according to claim 2 or 5 wherein the device is a transdermal drug delivery device comprising a backing layer, a permeation enhancer reservoir containing a permeation enhancer on the skin proximal side of the backing layer, a drug reservoir layer containing at least one drug to be transdermally administered on the skin proximal side of the permeation enhancer reservoir, and a means for maintaining said drug device in drug transmitting relation with the skin, wherein the rate controlling membrane is positioned between the permeation enhancer reservoir and the drug reservoir.

10. A rate controlling membrane according to claim 2 wherein the membrane comprises a material selected from the group consisting of polyurethanes or polyether blocked amides copolymers.

11. A rate controlling membrane according to claim 10 wherein the membrane is positioned in sealing relationship with an internal surface of one end of an impermeable reservoir of a fluid-imbibing drug delivery device, wherein said fluid imbibing drug delivery device comprises an impermeable reservoir containing a piston that divides the reservoir into a drug containing chamber and a water-swellable agent containing chamber, wherein the water-swellable agent containing chamber is provided with an outlet which accommodates said membrane.

12. A rate controlling membrane according to claim 11 wherein the drug containing chamber comprises leuprolide.

13. A rate controlling membrane according to claim 1 wherein the elevated temperature is about 45–80° C. and the predetermined period is about 1–75 hours.

14. A rate controlling membrane according to claim 1 wherein the membrane is cooled to ambient conditions before being incorporated into the delivery device.

15. A rate controlling membrane according to claim 3 wherein the elevated temperature is about 52–72° C. and the predetermined time is about 2–36 hours.

16. A rate controlling membrane according to claim 10 wherein the elevated temperature is about 55–75° C. and the predetermined time is about 12–48 hours.

17. A method for processing rate controlling membranes used in controlled drug delivery devices comprising:
   a) exposing the membrane to a predetermined temperature of from about 30° C. to about 5° C. below the melting temperature of the membrane polymer prior to combination with a drug containing component of said delivery device;
   b) maintaining the membrane at the predetermined temperature for a period of time of from about 1 to 250 hours; and
   c) incorporating said membrane into a controlled drug delivery device.

18. A method according to claim 17 wherein the predetermined temperature is from about 45° C. to 80° C.

19. A method according to claim 18 wherein the membrane is maintained at the predetermined temperature for a period of time of from about 1 to 75 hours.

20. A method according to claim 17 wherein the membrane is cooled to ambient conditions over a period of time of about 0.1–150 hours prior to incorporating the membrane into the device.

21. A method according to claim 17 wherein the membrane is incorporated into a transdermal drug delivery device and comprises an increased drug permeability compared to a non-annealed membrane of the same materials.

22. A method according to claim 17 wherein the membrane is formed from a material selected from the group consisting of ethylene vinyl acetate copolymers, polyethylene, ethylene copolymers, ethylene oxide copolymers, polyamides, cellulosic materials, polyurethanes, polyether blocked amides copolymers, and polyvinyl acetate.

23. A method according to claim 17 wherein the membrane is formed from ethylene vinyl acetate copolymer.

24. A method according to claim 23 wherein the membrane comprises 4–18% vinyl acetate.

25. A method according to claim 24 wherein the membrane comprises 5–12% vinyl acetate.

26. A method according to claim 24 wherein the predetermined temperature is about 52–72° C. and the period of time is about 2–36 hours.

27. A method according to claim 17 wherein the membrane is formed from high density polyethylene.

28. A method according to claim 17 wherein the membrane is allowed to set at ambient conditions for a period of at least about 12 hours after processing prior to exposing the membrane to said predetermined temperature.

29. A method according to claim 28 wherein the membrane is allowed to set at ambient conditions for a period of at least 48 hours after processing prior to exposing the membrane to said predetermined temperature.

30. A method according to claim 17 wherein the membrane comprises polyurethane.

31. A method according to claim 30 wherein the predetermined temperature is about 55–75° C. and the period of time is about 12–48 hours.

32. A method according to claim 31 wherein the membrane is positioned in sealing relationship with an internal surface of one end of an impermeable reservoir of a fluid-imbibing drug delivery device, wherein said fluid imbibing drug delivery device comprises an impermeable reservoir containing a piston that divides the reservoir into an active agent containing chamber and a water-swellable agent containing chamber, wherein the water-swellable agent containing chamber is provided with an outlet which accommodates said membrane.

33. A method according to claim 32 wherein the membrane is plug-shaped.

34. A rate controlling membrane for a controlled drug delivery device, wherein the membrane material consists of ethylene vinyl acetate copolymer having a vinyl acetate content of about 4–18%, and further wherein said membrane is characterized by a DSC profile having a primary peak at about 94–99° C. and a secondary peak at greater than about 50° C.

35. A rate controlling membrane for an osmotic pump of a fluid-imbibing drug delivery device characterized by being subjected to an elevated temperature of about 30° C. to about 5° C. below the melting temperature of the membrane polymer for a predetermined period of about 1–250 hours prior to combination with a drug containing component of said delivery device, wherein the membrane comprises a material selected from the group consisting of polyurethanes or polyether blocked amides copolymers, and further wherein fluid peimeability of said rate controlling membrane regulates imbibition of fluid into said osmotic pump.

* * * * *

UNITED STATES PATENT AND TRADEMARK OFFICE
CERTIFICATE OF CORRECTION

PATENT NO. : 6,375,978 B1
DATED : April 23, 2002
INVENTOR(S) : Lothar W. Kleiner et al.

It is certified that error appears in the above-identified patent and that said Letters Patent is hereby corrected as shown below:

Column 3,
Line 19, after "invention" and before "to" insert -- is --
Line 30, change "temperate" to -- temperature --
Line 30, change "300" to -- 30 --

Column 4,
Line 2, change "containg" to -- containing --
Line 36, change "—50– 150º C." to -- -50 - 150º C --
Line 40, change "—50– 150 C." to -- -50 - 150º C --

Column 5,
Line 17, change "$T_9$" to -- $T_g$ --
Line 67, after "for" delete "a"

Column 7,
Line 30, delete "layer"

Column 13,
Line 11, table 3, change "ANNEALLING" to -- ANNEALING --

Column 14,
Line 42, change the comma after "machine" to a period -- . --

Column 16,
Line 28, before "40" delete "plug"

Column 17,
Line 32, before "memebrane" change "the" to -- to --
Line 32, change "adnig" to -- a drug --
Line 37, before "membrane" change "the" to -- a --
Line 60, after "layer" and before "said" insert -- wherein --
Line 61, before "skin-proximal" change "the" to -- a --
Line 63, after "reservoir" and before "comprises" insert -- layer --

Column 18,
Line 37, before "membrane" change "the" to -- a --

UNITED STATES PATENT AND TRADEMARK OFFICE
CERTIFICATE OF CORRECTION

PATENT NO. : 6,375,978 B1
DATED : April 23, 2002
INVENTOR(S) : Lothar W. Kleiner et al.

It is certified that error appears in the above-identified patent and that said Letters Patent is hereby corrected as shown below:

Column 20,
Line 23, change "peimeability" to -- permeability --

Signed and Sealed this

Twenty-third Day of November, 2004

JON W. DUDAS
*Director of the United States Patent and Trademark Office*